(12) United States Patent
Scholle et al.

(10) Patent No.: US 12,135,330 B2
(45) Date of Patent: Nov. 5, 2024

(54) ARTICLES AND METHODS INVOLVING DETECTION OF BINDING

(71) Applicant: Charles River Laboratories International, Inc., Wilmington, MA (US)

(72) Inventors: Michael D. Scholle, Bolingbrook, IL (US); John Sherrill, San Diego, CA (US)

(73) Assignee: Charles River Laboratories International, Inc., Wilmington, MA (US)

( * ) Notice: Subject to any disclaimer, the term of this patent is extended or adjusted under 35 U.S.C. 154(b) by 1437 days.

(21) Appl. No.: 16/497,485

(22) PCT Filed: Mar. 28, 2018

(86) PCT No.: PCT/US2018/024821
§ 371 (c)(1),
(2) Date: Sep. 25, 2019

(87) PCT Pub. No.: WO2018/183482
PCT Pub. Date: Oct. 4, 2018

(65) Prior Publication Data
US 2020/0018769 A1    Jan. 16, 2020

Related U.S. Application Data

(60) Provisional application No. 62/480,161, filed on Mar. 31, 2017.

(51) Int. Cl.
| | |
|---|---|
| *G01N 33/68* | (2006.01) |
| *C40B 30/04* | (2006.01) |
| *H01J 49/16* | (2006.01) |
| *H01J 49/04* | (2006.01) |

(52) U.S. Cl.
CPC ......... *G01N 33/6851* (2013.01); *C40B 30/04* (2013.01); *H01J 49/164* (2013.01); *G01N 2610/00* (2013.01); *H01J 49/0418* (2013.01)

(58) Field of Classification Search
None
See application file for complete search history.

(56) References Cited

U.S. PATENT DOCUMENTS

| | | |
|---|---|---|
| 7,585,682 B2 | 9/2009 | Bamdad |
| 2003/0032043 A1 | 2/2003 | Pohl et al. |
| 2003/0106997 A1 | 6/2003 | Beecher et al. |
| 2003/0173513 A1 | 9/2003 | Koopmann et al. |
| 2005/0153454 A1 | 7/2005 | Chait et al. |
| 2005/0196791 A1 | 9/2005 | Koopman et al. |
| 2010/0112722 A1 | 5/2010 | Mrksich et al. |
| 2012/0220491 A1 | 8/2012 | Hutchens et al. |
| 2013/0089932 A1 | 4/2013 | Wu et al. |

FOREIGN PATENT DOCUMENTS

| | | | | |
|---|---|---|---|---|
| CA | 2682543 | * | 10/2008 | ........... G01N 33/543 |
| WO | WO 99/06833 A1 | | 2/1999 | |
| WO | WO 03/65043 A2 | | 8/2003 | |
| WO | WO 2008118959 | * | 10/2008 | ........... G01N 33/543 |

OTHER PUBLICATIONS

Restrepo, "Synthesis of pH-Sensitive Surfactants by the Terpolymerization of Methacrylic Acid, Methoxy Poly(ethylene glycol) Methacrylate, and Lauryl Methacrylate: Initiator Effect and Reactivity Ratio Study", Journal of Polymer Science : Part A: Poymer Chemistry, vol. 42, 2950-2959 (2004).*

Invitation to Pay Additional Fees for PCT/US18/24821 mailed May 31, 2018.

International Search Report and Written Opinion for PCT/US18/24821 mailed Jul. 20, 2018.

International Preliminary Report on Patentability for PCT/US18/24821 mailed Oct. 10, 2019.

Gurard-Levin et al., Combining Self-Assembled Monolayers and Mass Spectrometry for Applications in Biochips. Annu. Rev. Anal. Chem. 2008;1:767-800. Epub Mar. 28, 2008.

Gurard-Levin et al., High-Throughput Screening of Small Molecule Libraries using SAMDI Mass Spectrometry. ACS Comb. Sci. Jun. 2011;13:347-50.

Tsubery et al., Biochemical Assays of Immobilized Oligonucleotides with Mass Spectrometry. Langmuir. 2008;24:5433-8. Epub Apr. 12, 2008.

Vanderporten et al., Identification of Small-Molecule Noncovalent Binders Utilizing SAMDI Technology. SLAS Discovery. 2017;22(10):1211-7. Epub Jun. 5, 2017.

Yeo et al., Label-Free Detection of Protein-Protein Interactions on Biochips. Angew. Chem. Int. Ed. 2005;44:5480-3. Epub Jul. 29, 2005.

Patrie et al., Self-assembled monolayers for MALDI-TOF mass spectrometry for immunoassays of human protein antigens. Anal Chem. Aug. 1, 2007;79(15):5878-87. doi: 10.1021/ac0701738. Epub Jun. 28, 2007.

Ryan et al., Patterning multiple aligned self-assembled monolayers using light. Langmuir. Oct. 12, 2004;20(21):9080-8. doi: 10.1021/la048443u.

(Continued)

*Primary Examiner* — Ann Montgomery
(74) *Attorney, Agent, or Firm* — Wolf, Greenfield & Sacks, P.C.

(57) ABSTRACT

Articles and methods involving detection of binding between two or more species using MALDI are generally provided. In some embodiments, a method comprises exposing a first species to a composition comprising a second species, capturing the first species on a self-assembled monolayer, and performing MALDI on the self-assembled monolayer to generate a signal from the second species and a signal from a standard species present in the self-assembled monolayer. A ratio (first ratio) of the signal from the second species to the signal from the standard species may be compared to a cutoff value in order to determine if binding has occurred. This method may allow determination of a relative affinity of the second species for the first species.

20 Claims, 14 Drawing Sheets

(56) References Cited

OTHER PUBLICATIONS

Scholle et al., High-Throughput Affinity Selection Mass Spectrometry Using SAMDI-MS to Identify Small-Molecule Binders of the Human Rhinovirus 3C Protease. SLAS Discov. Sep. 2021;26(8):974-983. doi: 10.1177/24725552211023211. Epub Jun. 19, 2021.

* cited by examiner

ARTICLES AND METHODS INVOLVING DETECTION OF BINDING

RELATED APPLICATIONS

This application is a national stage filing under 35 U.S.C. § 371 of International Application No. PCT/US2018/024821, filed Mar. 28, 2018, which claims the benefit of U.S. Provisional Application No. 62/480,161, filed Mar. 31, 2017, the contents of each of which are incorporated herein by reference in its entirety.

FIELD

Articles and methods involving detection of binding between two or more species are generally provided.

BACKGROUND

MALDI can be a useful tool to identify whether or not a species with a known mass is present in a sample. In some cases, it can be challenging to identify how much of the species is present due to imprecision inherent in the technique. Accordingly, improved articles and methods related to performing MALDI in a quantitative or semi-quantitative manner would be beneficial.

SUMMARY

Articles and methods involving the detection of binding between two or more species, e.g., using MALDI, are generally provided. The subject matter disclosed herein involves, in some cases, interrelated products, alternative solutions to a particular problem, and/or a plurality of different uses of one or more systems and/or articles.

In one set of embodiments, methods are provided. Some methods are methods for detecting binding between a first species and a second species. Some methods are methods for comparing a relative affinity of a first small molecule for a target polypeptide to a relative affinity of a second small molecule for the target polypeptide. Some methods are methods of performing quality control on a MALDI instrument.

In some embodiments, a method comprises exposing a first species to a composition comprising a second species; capturing the first species on a self-assembled monolayer comprising a standard species; performing MALDI on the self-assembled monolayer to generate a signal from the second species and a signal from the standard species; and determining whether binding has occurred if a ratio of the signal from the second species to the signal from the standard species is greater than or equal to a cutoff value.

A method may comprise exposing a target polypeptide to a composition comprising at least a first small molecule and the second small molecule; capturing the target polypeptide on a self-assembled monolayer comprising a standard species; performing MALDI on the self-assembled monolayer to generate a signal from the first small molecule, a signal from the second small molecule, and a signal from the standard species; and comparing a first ratio to a second ratio to determine a relative affinity of the first small molecule for the target polypeptide and the second small molecule for the target polypeptide, wherein the first ratio comprises a ratio of the signal from the first small molecule to the signal from the standard species, and the second ratio comprises a ratio of the signal from the second small molecule to the signal from the standard species.

In some embodiments, a method comprises performing a MALDI measurement on a self-assembled monolayer comprising a known concentration of a standard species to generate a signal from the standard species; and determining whether an abnormality has occurred if the signal from the standard species is outside of a pre-determined range.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
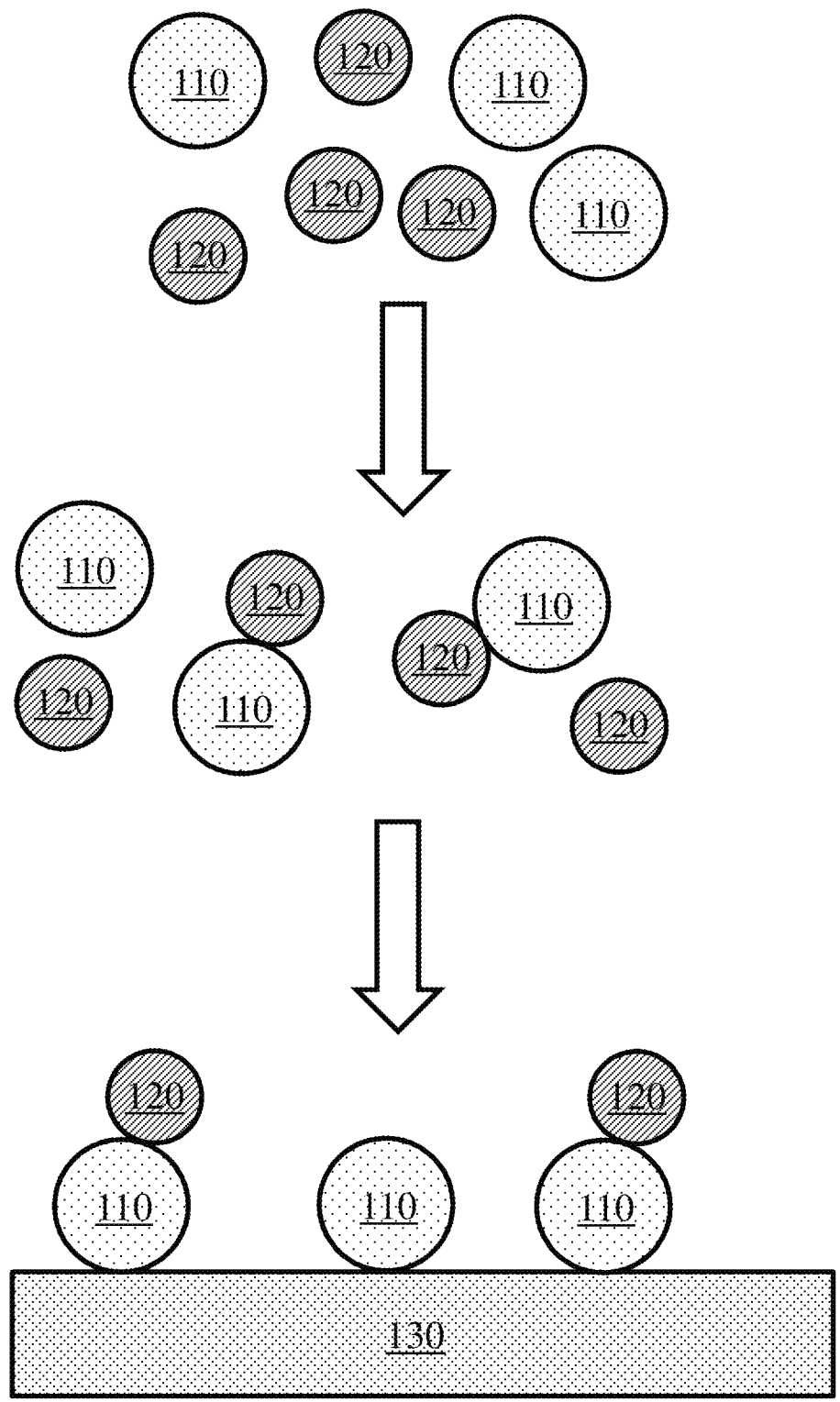
FIG. 1A shows a method for exposing a first species to a composition comprising a second species and then capturing the first species on a self-assembled monolayer, according to some embodiments.

Articles and methods related to detection of binding between a first species and a second species are generally provided. Certain articles and methods relate to reproducibly, quantitatively, and/or semi-quantitatively detecting an amount of binding using a mass spectroscopy technique, such as Matrix Assisted Laser Desorption/Ionization (MALDI) (which may optionally be coupled with Time Of Flight (TOF) detection). Binding may comprise covalent binding, may comprise non-covalent binding, and/or may comprise complex formation between at least two species.

During MALDI (e.g., MALDI-TOF) experiments performed on a sample, one or more signals may be generated from one or more species present in the sample. The signal generated from any given species may occur at a molecular weight that is indicative of the species, and may have an intensity or area under the curve (AUC) that bears some relationship to the amount and/or concentration of species in the sample. However, the intensity or AUC may not be directly related to the amount and/or concentration of species present in the sample and/or may vary during the experiment due to factors unrelated to the amount and/or concentration of the species, such as spread in the kinetic energy of the species after ionization and sample hot spots. This variation may make it challenging to compare signal intensity or AUC from one experiment to another and may make it difficult or impossible to correlate signal intensity or AUC with species amount and/or concentration.

The inventors have recognized these problems, and have developed inventive articles and methods that can use MALDI (e.g., MALDI-TOF) to generate signals from one or more species in a sample that have an intensity or AUC that is reproducibly, quantitatively, and/or semi-quantitatively correlated with the amount and/or concentration of the species in the sample. Certain methods described herein relate to ways to normalize signals generated from the species so that signals generated during different experiments or at different times during a single experiment may be compared to each other in a reliable manner. For example, MALDI may be used to analyze different samples on a single substrate or different samples on different substrates that are normalized such that it is possible to make meaningful comparisons between the samples. Some methods described herein relate to ways of performing quality control on a MALDI instrument so that a user can determine whether or not any abnormalities have occurred during measurement, such as abnormalities that may interfere with the generation of reliable signals.

In some embodiments, one or more signals generated during MALDI (e.g., MALDI-TOF) may be normalized by a signal arising from a substrate on which MALDI is performed, such as a self-assembled monolayer (SAM). For example, MALDI may be performed on a SAM that comprises one or more standard species from which a signal is generated. When the standard species is present at a known and uniform concentration in the SAM, variation in the intensity or AUC of the signal arising from the standard species between MALDI measurements may be assumed to be due to variations inherent in the MALDI process, and this variation may then be accounted for in the other signal(s) generated during the MALDI measurement. This may allow signals arising from species that are not the standard species to be compared to each other reproducibly, quantitatively, and/or semi-quantitatively. Normalizing signals from species of interest by a signal arising from a standard species that is part of a MALDI substrate may have certain advantages, including allowing for normalization based on a species that is present at a known and reproducible amount, allowing for normalization based on a species that would be present in or on the substrate under typical binding conditions, and/or being suitable for use during MALDI experiments (e.g., compatibility with MALDI experiments, not undergoing undesirable fragmentation, and the like). Other advantages may result from using a standard species that is a component of a SAM, such as having a molecular weight that is in the same range of a species giving to a signal to be normalized, being capable of binding to a conductive support and/or to a species to be detected or the binding partner of a species to be detected, and the like.

As another example, normalizing a signal from a species of interest by a signal arising from a standard species present in or on a substrate such as a SAM, or monitoring a signal arising from a standard species present in or on a substrate such as a SAM, may allow for facile quality control. If the signal from a standard species present in or on the SAM is outside of a pre-determined range, it may indicate to a user who is performing the MALDI (e.g., MALDI-TOF) measurement that the MALDI instrument is functioning abnormally. Because the signal from the standard species would be present in each MALDI measurement, this technique may allow for rapid detection of errors in instrument functionality and/or rapid detection of abnormalities associated with the SAM.

In some embodiments, normalized signals generated during a MALDI (e.g., MALDI-TOF) measurement may be used to determine whether or not binding between a first species or target species and a second species (e.g., between a polypeptide such as a protein and a small molecule, between two polypeptides such as two proteins, between two polynucleotides, between a polynucleotide and a small molecule) has occurred and/or the extent of binding between the first species and the second species. Methods employing normalized signals for this purpose generally comprise at least a step of exposing the first species to a composition comprising the second species and a step of capturing the first species for subsequent analysis. FIG. 1A shows one non-limiting embodiment of a process comprising first exposing a first species 110 to a composition comprising a second species 120 and then capturing first species 110 on a substrate (e.g., SAM) 130. The first species may be exposed to the composition comprising the second species by, for example, mixing the first species into the composition or mixing a composition comprising the first species with a composition comprising the second species. The first species may be captured on the SAM by forming a bond with one or more components of the SAM (e.g., forming a covalent bond and/or other type of bond with the first species) and/or interacting with one or more components of the SAM. When the first species is captured on the SAM, any molecules of the second species to which it is bound are also captured. If the first species does not bind to the second species, the second species is not captured. Binding between the first species and the second species may be of any suitable type, such as non-covalent binding, covalent binding, binding that comprises one the formation of one or more hydrogen bonds, and/or electrostatic interaction.

It should be noted that while FIG. 1A shows three steps (exposure, binding, and capture), the first two steps may be performed concurrently and/or as one step in some embodiments. It should also be noted that while FIG. 1A shows the SAM as a free-standing layer, in some embodiments the SAM may be disposed on a support (e.g., a conductive support). That is, the system and/or method may include additional components or steps that are not shown in the figures.

In some embodiments, one or more steps may be performed after or between one or more of the method steps shown in FIG. 1A. As an example, a first species (e.g., a target polypeptide such as a protein, a target polynucleotide, a target small molecule) may be captured on a SAM and an additional step of washing the SAM after capture may be performed. This step may remove any molecules of the first species which were not captured on the SAM and any other molecules (e.g., molecules of the second species) that had been deposited onto the SAM but which were not captured on the SAM or bound to the first species. Typically, a first species that is captured on a SAM is not removed from the SAM during typical washing conditions (e.g., washing with water, washing with a buffer).

Figure 1B:
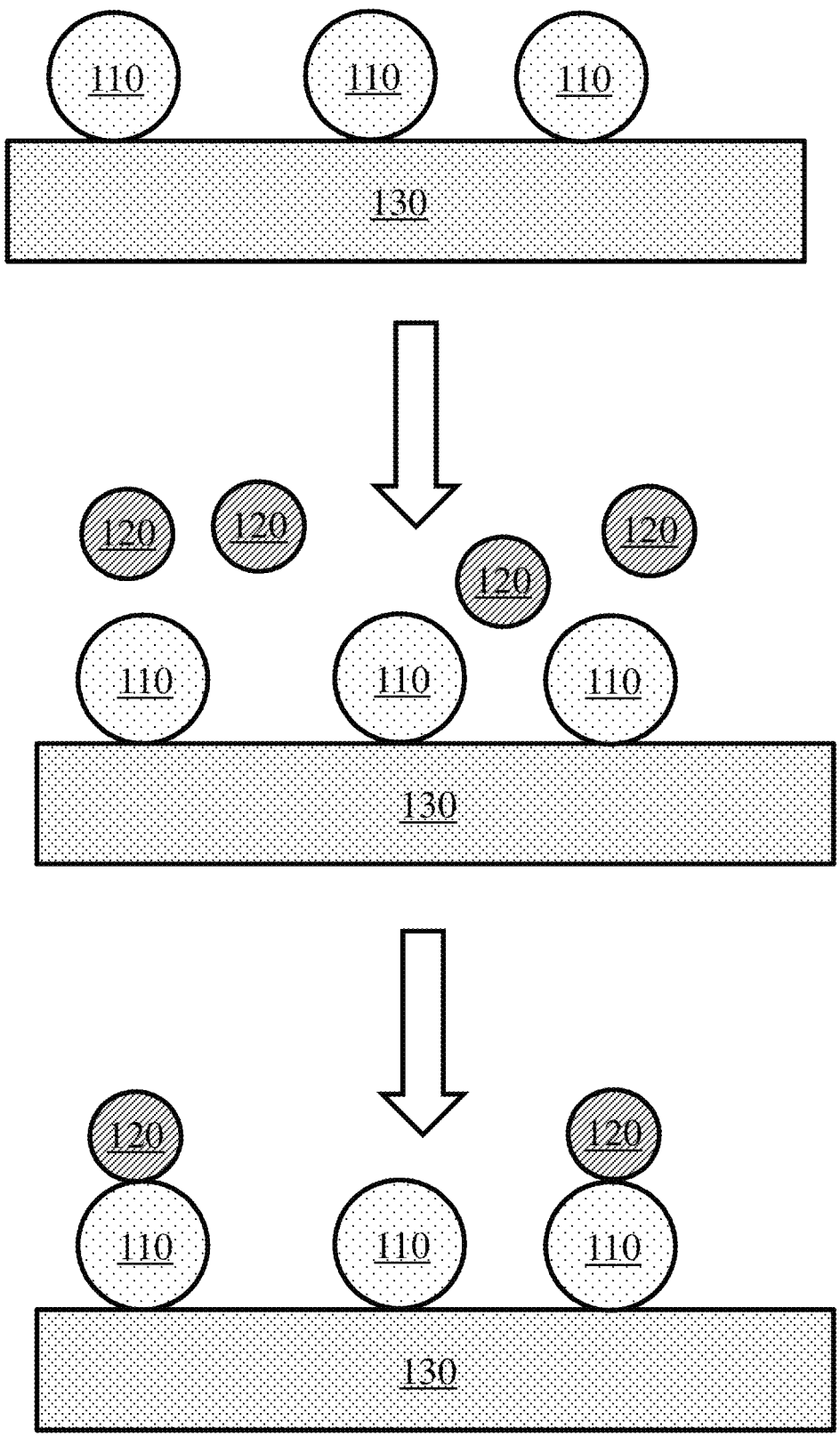
FIG. 1B shows a method for capturing a first species on a self-assembled monolayer and then exposing the first species to a composition comprising a second species, according to some embodiments.

In some embodiments, a first species (e.g., a target polypeptide such as a protein, a target polynucleotide, a target small molecule) may be captured on a SAM prior to exposure to a composition comprising a second species (e.g., a small molecule, a polypeptide such as a protein, a polynucleotide). FIG. 1B shows one non-limiting embodiment of a method for exposing first species 110 which is captured on SAM 130 to a composition comprising second species 120. As described above, it should be noted that while FIG. 1B shows two steps (exposure and capture), the these steps may be performed concurrently and/or as one step in some embodiments. In methods where the first species is captured prior to exposure to the composition comprising the second species, exposure may comprise applying the composition comprising the second species to the captured first species. The first species may be captured on the SAM prior to the method shown in FIG. 1B, and one or more optional washing steps may be performed prior to or after the method shown in FIG. 1B. For instance, a washing step may be performed prior to the method shown in FIG. 1B and after capture of the first species on the SAM. This washing step may remove any molecules of the first species which had been deposited on the SAM but not captured by the SAM. Then, any molecules of the second species that bind to the first species will bind to molecules of the first species that are captured by the SAM. In some embodiments, as described above in relation to FIG. 1A, one or more washing steps may be performed after exposure of the first species to the composition comprising the second species to remove any molecules of the second species that had been deposited onto the SAM but which were not captured on the SAM or bound to the first species. MALDI may be performed after each wash, and a decrease in the amount of the second species measured between two washes may be used to determine an amount of unbinding of the second species from the first species that occurred between the washes. If two or more washes are spaced at known time intervals, rates of unbinding of the second species from the first species may be obtained by, for example, dividing a measured amount of unbinding by a time interval between washes for each successive wash. Rates of unbinding of the second species from the first species may be compared across different environments using this technique (e.g., different samples comprising a second species bound to a captured first species may be exposed to different environments between washes).

Figure 1C:
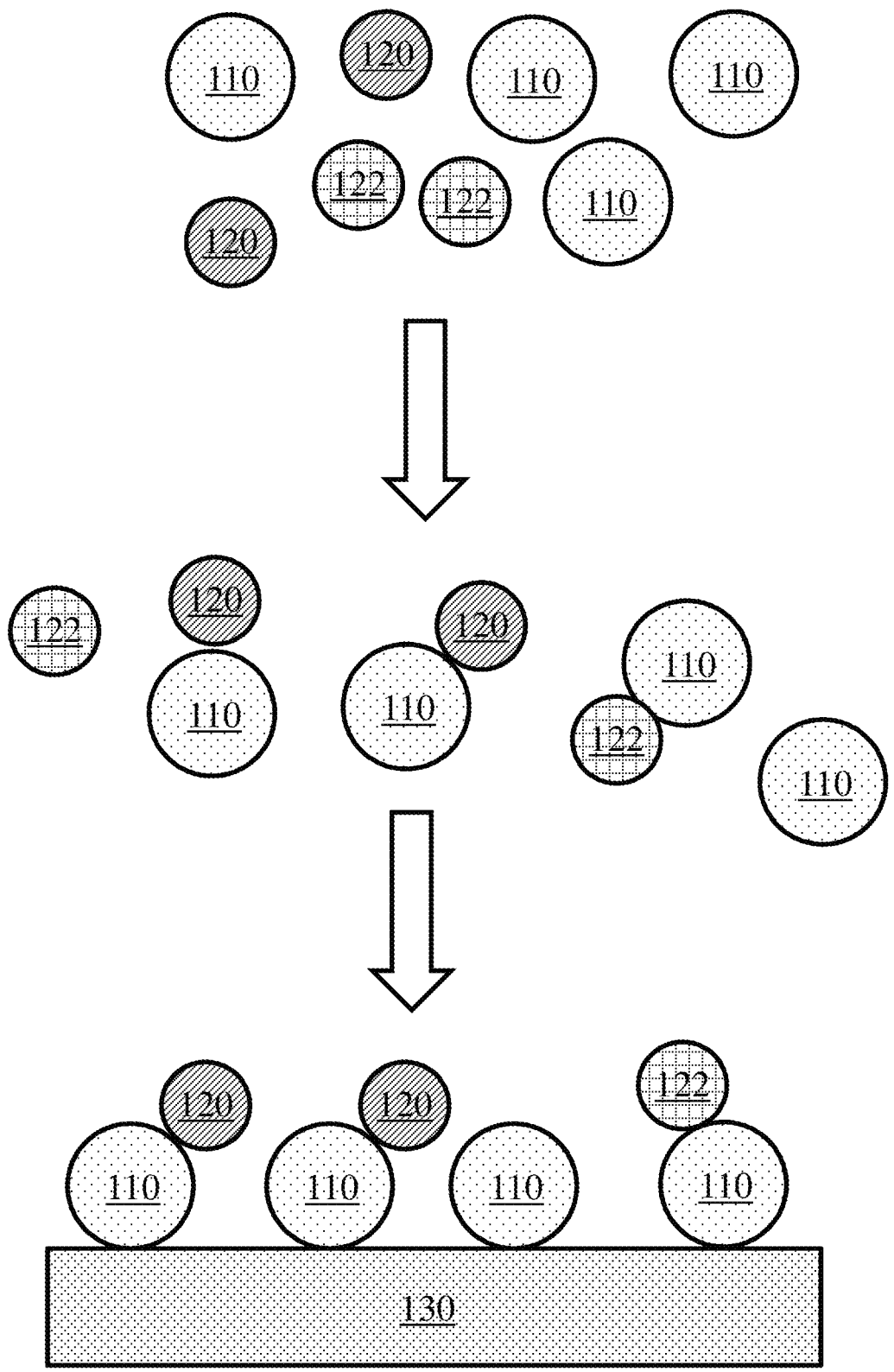
FIG. 1C shows a method for exposing a first species to a composition comprising a second species and a third species and capturing the first species on a self-assembled monolayer, according to some embodiments.

In certain embodiments, a first species (e.g., a target polypeptide such as a protein, a target polynucleotide, a target small molecule) may be exposed to a composition comprising at least a second species (e.g., a small molecule, a polypeptide such as a protein, a polynucleotide) and a third species (e.g., a small molecule, a polypeptide such as a protein, a polynucleotide). For instance, FIG. 1C shows an example of a method where first species 110 is exposed to a composition comprising second species 120 and a third species 122. The first species may bind to both the second species and the third species, only the second species, only the third species, or neither the second species nor the third species. In some embodiments, such as shown in FIG. 1C, the second species competes with the third species for binding to the first species. The relative affinity of the second species for the first species may be greater than the relative affinity of the third species for the first species, lower than the relative affinity of the third species for the first species, or equal to the relative affinity of the third species for the first species. In some embodiments, it may be possible for cooperative binding to occur between all three species. For instance, the first species may comprise a site at which the second species can bind and a site at which the third species can bind, the second species may comprise a site at which the first species can bind and a site at which the third species can bind, and/or the three species may bind together at a single site spread across the three species. In some embodiments, there may be both cooperative binding and competitive binding between the second species and the third species.

In some embodiments in which first species (e.g., a target polypeptide such as a protein, a target polynucleotide, a target small molecule) is exposed to a composition comprising at least a second species (e.g., a small molecule, a polypeptide such as a protein, a polynucleotide) and a third species (e.g., a polypeptide such as a protein, a polynucleotide), the third species may be a competitor species that competes for binding of the second species with the first species. The competitor species may not undergo capture on the SAM, or it may be captured on the SAM in an amount that is much lower than the first species. Molecules of the second species that bind to the competitor species are thus not captured on the SAM, or captured to a small degree on the SAM. The relative affinity of the second species for the competitor species may be greater than the relative affinity of the second species for the first species, lower than the relative affinity of the second species for the first species, or equal to the relative affinity of the second species for the first species. In some embodiments, a ratio of the amount of first species captured on the SAM to the amount of competitor species captured on the SAM may be greater than or equal to 5, greater than or equal to 10, greater than or equal to 20, greater than or equal to 50, greater than or equal to 100, greater than or equal to 200, or greater than or equal to 500. In some embodiments, a ratio of the amount of first species captured on the SAM to the amount of competitor species captured on the SAM may be less than or equal to 1000, less than or equal to 500, less than or equal to 200, less than or equal to 100, less than or equal to 50, less than or equal to 20, or less than or equal to 10. Combinations of the above-referenced ranges are also possible (e.g., greater than or equal to 5 and less than or equal to 500). Other ranges are also possible. It should also be noted that a composition may comprise more than one competitor species (e.g., at least two competitor species, at least three competitor species, at least four competitor species, or more competitor species).

As shown in FIG. 1C, in some embodiments, first species 110 may be captured on SAM 130 after being exposed to the composition. However, in other embodiments the first species may be captured on the SAM prior to exposure to the composition. It should also be noted that the composition may further comprise one or more additional species such as a fourth species, a fifth species, a sixth species, and/or other additional species. The additional species in the composition may bind to the first species or may not bind to the first species and may bind to the second species or not bind to the second species. The relative affinities of each species of the composition for the first species or the second species with respect to each other may be determined by methods described herein.

In some embodiments, MALDI (e.g., MALDI-TOF) may be performed on the SAM to determine the identity and/or amount of any species captured on the SAM. In some embodiments, one or more steps may optionally be performed prior to MALDI. For example, a matrix may optionally be applied to the SAM as well as any species captured on the SAM and/or the matrix may be bound to any species captured on the SAM. Without wishing to be bound by theory, the matrix may assist in vaporization of the SAM and any species captured thereon or bound to species captured thereon during MALDI, may increase the signal arising from any species captured on the SAM or bound to species captured on the SAM generated during MALDI, and/or may increase the ratio of the signal arising from any species captured on the SAM or bound to species captured on the SAM to noise generated during the MALDI. In some embodiments, the matrix may be applied after exposure of a first species (e.g., a target polypeptide such as a protein, a target polynucleotide, a target small molecule) to a composition comprising at least a second species (e.g., a small molecule, a polypeptide such as a protein, a polynucleotide) and/or a third species (e.g., a small molecule, a polypeptide such as a protein, a polynucleotide) and/or after capture of the first species on the SAM. In some embodiments, the matrix may be applied after a step of washing the SAM after exposure and capture.

Figure 2:
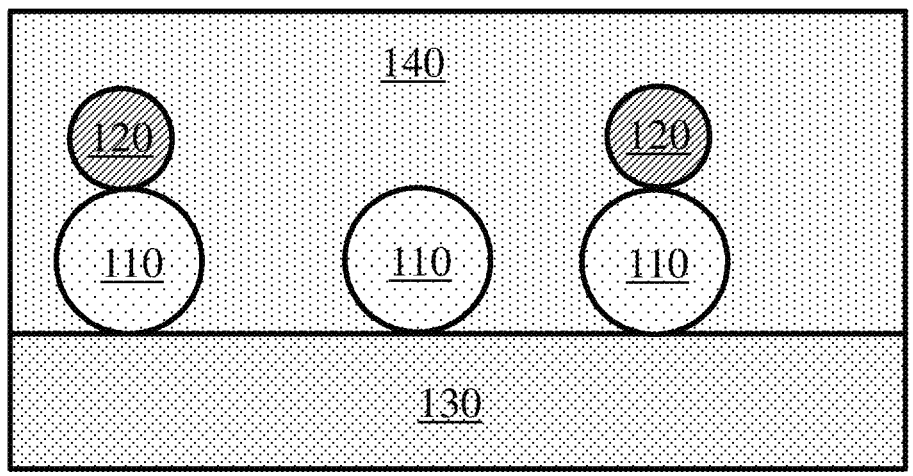
FIG. 2 shows a method for applying a matrix to a self-assembled monolayer, according to some embodiments.

FIG. 2 shows one non-limiting example of a method in which matrix 140 is applied to SAM 130 on which first species 110 has been captured. Although FIG. 2 shows the first species bound to a second species, it should be understood that the first species may be unbound to any component other than the SAM, or may be bound to more than one species (e.g., bound to a second species and bound to a third species).

As described above, in certain embodiments MALDI (e.g., MALDI-TOF) may be performed during one or more methods described herein. MALDI is an analysis method in which a sample is vaporized, ionized, and then accelerated to a mass spectrometer. The mass spectrometer may be a Time of Flight (TOF) spectrometer, where the ratio of the mass of each ion generated to the charge of the ion is measured by the time required for the ion to reach the detector. MALDI may be performed on a SAM on which one or more species has been captured (e.g., a first species and any second, third, or other species bound to the first species) or may be performed on a SAM on which no species has been captured.

When MALDI (e.g., MALDI-TOF) is performed, one or more signals are typically generated. The signals may include information regarding the mass of the species from which the signal arises, and may also include an intensity (usually understood to be the maximum intensity of the signal) and an AUC. Typically, the intensity and/or the AUC may be related to the concentration and/or amount of the species in the sample from which the signal arises. References herein to comparing normalized or unnormalized signals typically refer to comparing the intensity and/or the AUC of the normalized or unnormalized signals unless otherwise specified. Unless otherwise specified, the intensity of a signal should be understood to be the difference between the measured intensity of the signal and the measured baseline and the AUC of a signal should be understood to be the AUC of the portions of the signal that exceed the measured baseline.

In embodiments in which MALDI (e.g., MALDI-TOF) is performed on a SAM on which a species has been captured (e.g., a first species), a signal arising from the first species may be generated. If a second, third, or other species is bound to a captured first species, MALDI may be used to generate a signal from these additional species. The signals generated during MALDI typically carry information related to the mass of the species from which the signal arises, and so can be used to determine the identity of the species from which the signal arises. The presence or absence of signals from the additional species may, in some cases, be used to determine whether the additional species were bound to the first species during the exposure step. This method for detecting binding may have several advantages, such as allowing for the direct detection of binding, the detection of binding without the use of a label and/or the detection of binding under one or more conditions of interest prior to capture (e.g., detection of binding at a desired concentration of a first species and a second species and/or any additional species, detection of binding between a first species and a second species in the presence of a third species, detection of binding under physiological conditions).

When a MALDI (e.g., MALDI-TOF) measurement is performed on a SAM, signals from components of the SAM are also typically generated. For example, if the SAM comprises a standard species a signal from the standard species may be generated during MALDI. The signal arising from the SAM and any standard species therein typically experiences variation in intensity and AUC arising from inherent uncertainty in MALDI that is substantially similar to the variation in intensity and AUC arising from inherent uncertainty in MALDI that is experienced by any species captured on the SAM or bound to a species captured on the SAM. For this reason, signals arising from non-standard species during the MALDI measurement may be normalized by the signal arising from the standard species in order to obtain a consistently normalized signal. Signals from non-standard species are typically normalized after subtracting any intensity or AUC that arises from the baseline for the signal arising from the non-standard species and subtracting any intensity or AUC that arises from the baseline for the signal arising from the standard species.

Normalizing may be performed by any suitable means. In some embodiments, normalization is performed by determining a ratio of the signal arising from a species (e.g., a first species, a second species a third species) to the signal arising from the standard species. In some embodiments, the normalized signal (e.g., a ratio of a signal arising from a species to a signal arising from the standard species) may be compared to a pre-determined value (e.g., a cutoff value to determine whether or not binding has occurred) or may be compared to a relative value (e.g., a value obtained from a signal arising from a different MALDI measurement, a different signal arising from the same measurement).

For example, a normalized signal may be used to compare the binding of a second species (e.g., a small molecule, a polypeptide such as a protein, a polynucleotide) to a first species (e.g., a target polypeptide such as a protein, a target polynucleotide, a target small molecule) under a variety of conditions (e.g., pH, concentration, presence of additional species that may bind to the first species) in order to understand how the binding of the second species to the first species varies with these conditions. As an example, a normalized signal arising from the second species (e.g., a ratio of the signal from the second species to the signal from a standard species) may be compared to a cutoff value to determine whether or not binding has occurred for any particular condition. Cutoff values may be selected as desired, and are typically values of intensity or AUC at which the intensity or AUC exceeds the baseline by a certain amount and/or exceeds the baseline by a certain multiple of the average noise of the baseline. The average noise of the baseline is typically determined by MALDI software. The cutoff value may be a value of intensity or AUC at which the intensity or AUC exceed the baseline by greater than or equal to 1%, greater than or equal to 3%, greater than or equal to 5%, greater than or equal to 10%, greater than or equal to 20%, greater than or equal to 50%, or greater than or equal to 100%. The cutoff value may be a value of intensity or AUC at which the intensity or AUC exceed the baseline by less than or equal to 200%, less than or equal to 100%, less than or equal to 50%, less than or equal to 20%, less than or equal to 10%, less than or equal to 5%, or less than or equal to 3%. Combinations of the above-referenced ranges are also possible (e.g., greater than or equal to 1% and less than or equal to 200%, or greater than or equal to 3% and less than or equal to 200%). Other ranges are also possible.

The cutoff value may be a value of intensity or AUC at which the intensity or AUC is greater than or equal to 2 times greater than the average noise of the baseline, greater than or equal to 5 times greater than the average noise of the baseline, greater than or equal to 10 times greater than the average noise of the baseline, greater than or equal to 20 times greater than the average noise of the baseline, greater than or equal to 50 times greater than the average noise of the baseline, greater than or equal to 100 times greater than the average noise of the baseline, greater than or equal to 200 times greater than the average noise of the baseline, greater than or equal to 500 times the average noise of the baseline, or greater than or equal to 1000 times greater than the average noise of the baseline. The cutoff value may be a value of intensity or AUC at which the intensity or AUC is less than or equal to 2000 times greater than the average noise of the baseline, less than or equal to 1000 times greater than the average noise of the baseline, less than or equal to 500 times greater than the average noise of the baseline, 200 times greater than the average noise of the baseline, less than or equal to 100 times greater than the average noise of the baseline, less than or equal to 50 times greater than the average noise of the baseline, less than or equal to 20 times greater than the average noise of the baseline, less than or equal to 10 times greater than the average noise of the baseline, or less than or equal to 5 times greater than the average noise of the baseline. Combinations of the above-referenced ranges are also possible (e.g., greater than or equal to 2 times and less than or equal to 2000 times the average noise of the baseline, greater than or equal to 2 times and less than or equal to 200 times greater than the average noise of the baseline). Other ranges are also possible.

As another example, experiments may be performed in which the first species (e.g., a target polypeptide such as a protein, a target polynucleotide, a target small molecule) is exposed to a variety of compositions, each of which comprise the second species (e.g., a small molecule, a polypeptide such as a protein, a polynucleotide) at a different concentration. The signals arising from these experiments may be normalized (e.g., by taking a ratio of the intensity or AUC of the signal to the intensity or AUC of a signal from a standard species) and/or compared to each other to formulate an expression for the amount of binding as a function of concentration of the second species, to determine the minimum concentration of the second species at which binding occurs, to determine the maximum amount of binding that may occur between the second species and the first species, and/or to determine the concentration of the second species at which a certain percentage (e.g., 10%, 25%, 50%, 75%, or 90%) of the maximum binding occurs. In some embodiments, a method described herein may be capable of determining the concentration of the second species at which a certain percentage (e.g., 10%, 25%, 50%, 75%, or 90%) of the maximum binding occurs when this concentration is less than or equal to 100 millimolar, less than or equal to 10 millimolar, less than or equal to 1 millimolar, less than or equal to 100 micromolar, less than or equal to 10 micromolar, less than or equal to 1 micromolar, less than or equal to 100 nanomolar, less than or equal to 10 nanomolar, less than or equal to 1 nanomolar, less than or equal to 100 femtomolar, less than or equal to 50 femtomolar, less than or equal to 20 femtomolar, less than or equal to 10 femtomolar, less than or equal to 5 femtomolar, or less than or 1 femtomolar. In some embodiments, a method described herein may be capable of determining the concentration of the second species at which a certain percentage (e.g., 10%, 25%, 50%, 75%, or 90%) of the maximum binding occurs when this concentration is greater than or equal to 0.1 femtomolar, greater than or equal to 1 femtomolar, greater than or equal to 10 femtomolar, greater than or equal to 100 femtomolar, greater than or equal to 1 nanomolar, greater than or equal to 10 nanomolar, greater than or equal to 100 nanomolar, greater than or equal to 1 micromolar, greater than or equal to 10 micromolar, greater than or equal to 100 micromolar, greater than or equal to 1 millimolar, or greater than or equal to 10 millimolar. Combinations of the above-referenced ranges are also possible (e.g., greater than or equal to 0.1 femtomolar and less than or equal to 100 millimolar). Other ranges are also possible.

As a third example, experiments may be performed in which a first species (e.g., a target polypeptide such as a protein, a target polynucleotide) is exposed to a variety of compositions, each of which comprise a different mixture of additional species (e.g., small molecules, polypeptides such as a proteins, polynucleotides, a target small molecule). The relative affinities of the additional species for the first species may be compared to one another by normalization (e.g., by taking a ratio of the intensity or AUC of the signal of the species of interest to the intensity or AUC of a signal from a standard species). In some embodiments, these values may be quantitatively compared across experiments, and/or the relative affinity for a given additional species may be compared across different compositions.

As a fourth example, an experiment may be performed in which a first species (e.g., a target polypeptide such as a protein, a target polynucleotide, a target small molecule) is exposed to a composition comprising at least a second species (e.g., a small molecule, a polypeptide such as a protein, a polynucleotide) and a third species (e.g., a small molecule, a polypeptide such as a protein, a polynucleotide). A normalized signal from the second species (e.g., a ratio of the signal from the second species to the signal from a standard species) may be compared to a normalized signal from the third species (e.g., a ratio of the signal from the second species to the signal from a standard species) to determine a relative affinity of the second species for the first species and a relative affinity of the third species for the first species. In other words, determining the relative affinity of the second species for the first species and the third species for the first species may comprise comparing a first ratio (e.g., a ratio of the signal from the second species to the signal from the standard species) to a second ratio (e.g., a ratio of the signal from the third species to the signal from the standard species). If the wt % of the second species in the composition is equal to the wt % of the third species in the composition, the species with the larger normalized signal may have a higher relative affinity for the first species. However, other exposure conditions are also contemplated and in some embodiments the species with the smaller normalized signal may have a higher relative affinity for the first species (e.g., in the condition where the wt % in the composition of the species with the smaller normalized signal is substantially higher than the wt % in the composition of the species with a larger normalized signal).

In certain embodiments, a signal, a signal intensity, or the AUC of a signal arising from the SAM itself may be compared to one or more values. For example, a signal, a signal intensity, or the AUC of a signal arising from a standard species present within the SAM may be compared to a pre-determined range in order to determine whether or not an abnormality has occurred during the measurement. The pre-determined range may be a range indicative of the signal, signal intensity, and/or signal AUC typically observed during standard MALDI (e.g., MALDI-TOF) operation. In some embodiments, the pre-determined range for the standard species may span greater than or equal to one standard deviation, greater than or equal to two standard deviations, or greater than or equal to three standard deviations above and below an average intensity and/or average AUC observed for the standard species during typical MALDI operation. In some embodiments, the pre-determined range for the standard species may span less than or equal to four standard deviations, less than or equal to three standard deviations, or less than or equal to two standard deviations above and below an average intensity and/or average AUC observed for the standard species during typical MALDI operation. Combinations of the above-referenced ranges are also possible (e.g., greater than or equal to one standard deviation and less than or equal to four standard deviations). Other ranges are also possible.

In some embodiments, one or more signals generated during a MALDI (e.g., a MALDI-TOF) experiment may be monitored to determine whether or not an abnormality has occurred during preparation of a composition comprising at least a second species, preparation of the first species, exposure, binding, capture, washing, and/or any other step that may be performed in combination with the methods described herein. As an example, a control species (e.g., a small molecule, a polypeptide such as a protein, a polynucleotide) may be present at a known concentration in one or more of a composition, a wash fluid, a fluid that is a carrier fluid for any of the components or species described herein, and the like. In some embodiments, the control species may be captured on the SAM at a known concentration or may bind with a known affinity to a species that is captured on the SAM at a known concentration. A signal, signal intensity, and/or AUC of a signal from the control species may optionally be normalized by a signal intensity, and/or AUC of a signal from a standard species. The (normalized or unnormalized) signal, signal intensity, and/or AUC of a signal from the control species may be compared to a pre-determined range in order to determine whether or not an abnormality has occurred during the performance of any of the methods described herein. The abnormality may be related to the amount of control species captured on the SAM or detected by a MALDI measurement performed on the SAM, and may be related to exposure, binding, capture, washing, performance of a MALDI (e.g., MALDI-TOF) measurement, and the like. In some embodiments, the pre-determined range for the control species may be a range indicative of the signal, signal intensity, and/or signal AUC typically observed during standard MALDI operation. In some embodiments, the pre-determined range for the control species may span greater than or equal to one standard deviation, greater than or equal to two standard deviations, or greater than or equal to three standard deviations above and below an average intensity and/or average AUC observed for the control species during typical MALDI operation. In some embodiments, the pre-determined range for the control species may span less than or equal to four standard deviations, less than or equal to three standard deviations, or less than or equal to two standard deviations above and below an average intensity and/or average AUC observed for the control species during standard MALDI operation. Combinations of the above-referenced ranges are also possible (e.g., greater than or equal to one standard deviation and less than or equal to four standard deviations). Other ranges are also possible.

As described above, some embodiments relate to a first species that may be exposed to a composition and/or captured on a SAM. The first species may be a target for binding by an additional species (e.g., a second species, a third species). In some embodiments, the first species may comprise a biological molecule, such as a target polypeptide (e.g., a target protein such as β-secretase and/or dual leucine zipper kinase), and/or a target polynucleotide (e.g., an oligonucleotide, DNA, RNA). In some embodiments, the biological molecule may be functionalized with a group that assists in capture of the first species, such as a biotin group, a streptavidin group, an epitope tag (e.g., His6, FLAG, HA), a glutathione-s-transferase group, a strep tag, a myc tag, a green fluorescent protein group, a HaloTag, a SNAP-tag, a CLIP-tag, and/or a cutinase fusion group. For example, the biological molecule may be a biotinylated protein. Other compositions of the first species are also possible.

As also described above, certain embodiments may comprise exposing a first species to a composition comprising at least a second species (e.g., a small molecule, a polypeptide such as a protein, a polynucleotide). In some embodiments, the second species makes up greater than or equal to 0.1 wt % of the composition, greater than or equal to 0.2 wt % of the composition, greater than or equal to 0.5 wt % of the composition, greater than or equal to 1 wt % of the composition, greater than or equal to 2 wt % of the composition, greater than or equal to 5 wt % of the composition, greater than or equal to 10 wt % of the composition, greater than or equal to 20 wt % of the composition, greater than or equal to 50 wt % of the composition, or greater than or equal to 75 wt % of the composition. In some embodiments, the second species makes up less than or equal to 100 wt % of the composition, less than or equal to 75 wt % of the composition, less than or equal to 50 wt % of the composition, less than or equal to 20 wt % of the composition, less than or equal to 10 wt % of the composition, less than or equal to 5 wt % of the composition, less than or equal to 2 wt % of the composition, less than or equal to 1 wt % of the composition, less than or equal to 0.5 wt % of the composition, or less than or equal to 0.2 wt % of the composition. Combinations of the above-referenced ranges are also possible (e.g., greater than or equal to 0.1 wt % and less than or equal to 20 wt % of the composition, or greater than or equal to 0.1 wt % and less than or equal to 100 wt % of the composition). Other ranges are also possible.

In embodiments in which a first species (e.g., a target polypeptide such as a protein, a target polynucleotide, a target small molecule) is exposed to a composition comprising at least a second species, the second species may be any suitable material. In some embodiments, the second species may comprise a biological molecule, such as a polypeptide (e.g., a peptide, a protein such as β-secretase and/or dual leucine zipper kinase), and/or a polynucleotide (e.g., an oligonucleotide, DNA, RNA). In some embodiments, the second species may be a small molecule. Non-limiting examples of small molecules include sugars, nucleotides, and amino acids. In some embodiments, a small molecule may further comprise a biotin group.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

In some embodiments, a first species (e.g., a target polypeptide such as a protein, a target polynucleotide) may be exposed to a composition comprising at least a second species (e.g., a small molecule, a polypeptide such as a protein, a polynucleotide) and a third species (e.g., a small molecule, a polypeptide such as a protein, a polynucleotide). In some embodiments, the third species may make up greater than or equal to 0.1 wt % of the composition, greater than or equal to 0.2 wt % of the composition, greater than or equal to 0.5 wt % of the composition, greater than or equal to 1 wt % of the composition, greater than or equal to 2 wt % of the composition, greater than or equal to 5 wt % of the composition, greater than or equal to 10 wt % of the composition, greater than or equal to 20 wt % of the composition, greater than or equal to 50 wt % of the composition, or greater than or equal to 75 wt % of the composition. In some embodiments, the third species makes up less than or equal to 100 wt % of the composition, less than or equal to 75 wt % of the composition, less than or equal to 50 wt % of the composition, less than or equal to 20 wt % of the composition, less than or equal to 10 wt % of the composition, less than or equal to 5 wt % of the composition, less than or equal to 2 wt % of the composition, less than or equal to 1 wt % of the composition, less than or equal to 0.5 wt % of the composition, or less than or equal to 0.2 wt % of the composition. Combinations of the above-referenced ranges are also possible (e.g., greater than or equal to 0.1 wt % and less than or equal to 20 wt % of the composition, or greater than or equal to 0.1 wt % and less than or equal to 100 wt % of the composition). Other ranges are also possible.

In embodiments in which a first species (e.g., a target polypeptide such as a protein, a target polynucleotide, a target small molecule) is exposed to a composition comprising at least a second species (e.g., a small molecule, a polypeptide such as a protein, a polynucleotide) and a third species (e.g., a small molecule, a polypeptide such as a protein, a polynucleotide), a ratio of the wt % of the second species in the composition to the wt % of the third species in the composition may be greater than or equal to 0.01, greater than or equal to 0.02, greater than or equal to 0.05, greater than or equal to 0.1, greater than or equal to 0.2, greater than or equal to 0.5, greater than or equal to 1, greater than or equal to 2, greater than or equal to 5, greater than or equal to 10, greater than or equal to 20, or greater than or equal to 50. The ratio of the wt % of the second species in the composition to the wt % of the third species in the composition may be less than or equal to 100, less than or equal to 50, less than or equal to 20, less than or equal to 10, less than or equal to 5, less than or equal to 2, less than or equal to 1, less than or equal to 0.5, less than or equal to 0.2, less than or equal to 0.1, less than or equal to 0.005, or less than or equal to 0.002. Combinations of the above-referenced ranges are also possible (e.g., greater than or equal to 0.1 and less than or equal to 10, or greater than or equal to 0.01 and less than or equal to 100). Other ranges are also possible.

In embodiments in which a first species (e.g., a target polypeptide such as a protein, a target polynucleotide, a target small molecule) is exposed to a composition comprising at least a second species (e.g., a small molecule, a polypeptide such as a protein, a polynucleotide) and a third species, the third species may be any suitable material. In some embodiments, the third species may comprise a biological molecule, such as a polypeptide (e.g., a protein such as (3-secretase and/or dual leucine zipper kinase), and/or a polynucleotide (e.g., an oligonucleotide, DNA, RNA). In some embodiments, the third species may be a small molecule. Non-limiting examples of small molecules include sugars, nucleotides, and amino acids. In some embodiments, a small molecule may further comprise a biotin group. In some embodiments, both the second species and the third species may be small molecules.

In some embodiments, a first species (e.g., a target polypeptide such as a protein, a target polynucleotide, a target small molecule) may be exposed to a composition comprising at least a second species (e.g., a small molecule, a polypeptide such as a protein, a polynucleotide) and the composition may further comprise a surfactant. In some embodiments, the surfactant may make up greater than or equal to 0.001 wt % of the composition, greater than or equal to 0.002 wt % of the composition, greater than or equal to 0.005 wt % of the composition, greater than or equal to 0.01 wt % of the composition, greater than or equal to 0.02 wt % of the composition, greater than or equal to 0.05 wt % of the composition, greater than or equal to 0.1 wt % of the composition, greater than or equal to 0.2 wt % of the composition, greater than or equal to 0.5 wt % of the composition, greater than or equal to 1 wt % of the composition, greater than or equal to 2 wt % of the composition, or greater than or equal to 5 wt % of the composition. In some embodiments, the surfactant may make up less than or equal to 10 wt % of the composition, less than or equal to 2 wt % of the composition, less than or equal to 1 wt % of the composition, less than or equal to 0.5 wt % of the composition, less than or equal to 0.2 wt % of the composition, less than or equal to 0.1 wt % of the composition, less than or equal to 0.05 wt % of the composition, less than or equal to 0.02 wt % of the composition, less than or equal to 0.01 wt % of the composition, less than or equal to 0.005 wt % of the composition, or less than or equal to 0.002 wt % of the composition. Combinations of the above-referenced ranges are also possible (e.g., greater than or equal to 0.001 wt % and less than or equal to 10 wt % of the composition). Other ranges are also possible. Non-limiting examples of suitable surfactants include Tween 20, Triton X-100, and sodium dodecyl sulfate (SDS).

In some embodiments, a first species (e.g., a target polypeptide such as a protein, a target polynucleotide, a target small molecule) may be exposed to a composition comprising at least a second species (e.g., a small molecule, a polypeptide such as a protein, a polynucleotide) and the composition may further comprise one or more agents capable of reducing non-specific binding to the SAM. In some embodiments, the agent(s) capable of reducing non-specific binding of a species to the SAM may make up greater than or equal to 0.001 wt % of the composition, greater than or equal to 0.002 wt % of the composition, greater than or equal to 0.005 wt % of the composition, greater than or equal to 0.01 wt % of the composition, greater than or equal to 0.02 wt % of the composition, greater than or equal to 0.05 wt % of the composition, greater than or equal to 0.1 wt % of the composition, greater than or equal to 0.2 wt % of the composition, greater than or equal to 0.5 wt % of the composition, greater than or equal to 1 wt % of the composition, greater than or equal to 2 wt % of the composition, or greater than or equal to 5 wt % of the composition. In some embodiments, the agent(s) capable of reducing non-specific binding of a species to the SAM may make up less than or equal to 10 wt % of the composition, less than or equal to 5 wt % of the composition, less than or equal to 2 wt % of the composition, less than or equal to 1 wt % of the composition, less than or equal to 0.5 wt % of the composition, less than or equal to 0.2 wt % of the composition, less than or equal to 0.1 wt % of the composition, less than or equal to 0.05 wt % of the composition, less than or equal to 0.02 wt % of the composition, less than or equal to 0.01 wt % of the composition, or less than or equal to 0.005 wt % of the composition, less than or equal to 0.002 wt % of the composition. Combinations of the above-referenced ranges are also possible (e.g., greater than or equal to 0.001 wt % and less than or equal to 10 wt % of the composition). Non-limiting examples of possible agents capable of reducing non-specific binding include proteins such as bovine skin gelatin, bovine serum albumin, and bovine gamma globulin.

In some embodiments, a first species (e.g., a target polypeptide such as a protein, a target polynucleotide, a target small molecule) may be exposed to a composition comprising at least a second species (e.g., a small molecule, a polypeptide such as a protein, a polynucleotide) and the composition may further comprise a salt. In some embodiments, the salt may make up greater than or equal to 0.001 wt % of the composition, greater than or equal to 0.002 wt % of the composition, greater than or equal to 0.005 wt % of the composition, greater than or equal to 0.01 wt % of the composition, greater than or equal to 0.02 wt % of the composition, greater than or equal to 0.05 wt % of the composition, greater than or equal to 0.1 wt % of the composition, greater than or equal to 0.2 wt % of the composition, greater than or equal to 0.5 wt % of the composition, greater than or equal to 1 wt % of the composition, greater than or equal to 2 wt % of the composition, or greater than or equal to 5 wt % of the composition. In some embodiments, the salt may make up less than or equal to 10 wt % of the composition, less than or equal to 5 wt % of the composition, less than or equal to 2 wt % of the composition, less than or equal to 1 wt % of the composition, less than or equal to 0.5 wt % of the composition, less than or equal to 0.2 wt % of the composition, less than or equal to 0.1 wt % of the composition, less than or equal to 0.05 wt % of the composition, less than or equal to 0.02 wt % of the composition, less than or equal to 0.01 wt % of the composition, or less than or equal to 0.005 wt % of the composition, less than or equal to 0.002 wt % of the composition. Combinations of the above-referenced ranges are also possible (e.g., greater than or equal to 0.001 wt % and less than or equal to 10 wt % of the composition). Non-limiting examples of salts include chloride salts (e.g., sodium chloride, potassium chloride, magnesium chloride, manganese chloride, ammonium chloride) and phosphate salts (e.g., potassium phosphate, sodium phosphate).

In some embodiments, a first species (e.g., a target polypeptide such as a protein, a target polynucleotide, a target small molecule) may be exposed to a composition that comprises at least a second species (e.g., a small molecule, a polypeptide such as a protein, a polynucleotide) and comprises water or is an aqueous solution. The pH of the composition may be greater than or equal to 1.0, greater than or equal to 2.0, greater than or equal to 3.0, greater than or equal to 4.0, greater than or equal to 5.0, greater than or equal to 6.0, greater than or equal to 7.0, greater than or equal to 8.0, greater than or equal to 9.0, greater than or equal to 10.0, or greater than or equal to 11.0. The pH of the composition may be less than or equal to 12.0, less than or equal to 11.0, less than or equal to 10.0, less than or equal to 9.0, less than or equal to 8.0, less than or equal to 7.0, less than or equal to 6.0, less than or equal to 5.0, less than or equal to 4.0, less than or equal to 3.0, or less than or equal to 2.0. Combinations of the above-referenced ranges are also possible (e.g., greater than or equal to 1.0 and less than or equal to 12.0). Other ranges are also possible.

In some embodiments, a first species (e.g., a target polypeptide such as a protein, a target polynucleotide, a target small molecule) may be exposed to a composition that comprises at least a second species (e.g., a small molecule, a polypeptide such as a protein, a polynucleotide) and comprises a buffer. Non-limiting examples of suitable buffers include sodium acetate buffers, tris buffers, CHAPS buffers, CHES buffers, MES buffers, Bis-Tris buffers, HEPES buffers, bicine buffers, glycine buffers, CAPS buffers, and potassium phosphate buffers.

As described above, in certain embodiments a first species (e.g., a target polypeptide such as a protein, a target polynucleotide, a target small molecule) may be captured on a SAM. In some embodiments, the SAM may comprise one or more species that is capable of capturing the first species. In some embodiments, the species capable of capturing the first species may be present at a concentration in the SAM of greater than or equal to 0.001 mol % of the SAM, greater than or equal to 0.002 mol % of the SAM, greater than or equal to 0.005 mol % of the SAM, greater than or equal to 0.01 mol % of the SAM, greater than or equal to 0.02 mol % of the SAM, greater than or equal to 0.05 mol % of the SAM, greater than or equal to 0.1 mol % of the SAM, greater than or equal to 0.2 mol % of the SAM, greater than or equal to 0.5 mol % of the SAM, greater than or equal to 1 mol % of the SAM, greater than or equal to 2 mol % of the SAM, greater than or equal to 5 mol % of the SAM, greater than or equal to 10 mol % of the SAM, greater than or equal to 20 mol % of the SAM, or greater than or equal to 50 mol % of the SAM. In some embodiments, the species capable of capturing the first species may be present at a concentration in the SAM of less than or equal to 100 mol % of the SAM, less than or equal to 50 mol % of the SAM, less than or equal to 20 mol % of the SAM, less than or equal to 10 mol % of the SAM, less than or equal to 5 mol % of the SAM, less than or equal to 2 mol % of the SAM, less than or equal to 1 mol % of the SAM, less than or equal to 0.5 mol % of the SAM, less than or equal to 0.2 mol % of the SAM, less than or equal to 0.1 mol % of the SAM, less than or equal to 0.05 mol % of the SAM, less than or equal to 0.02 mol % of the SAM, less than or equal to 0.01 mol % of the SAM, less than or equal to 0.005 mol % of the SAM, or less than or equal to 0.002 mol % of the SAM. Combinations of the above-referenced ranges are also possible (e.g., greater than or equal to 0.001 mol % of the SAM and less than or equal to 100 mol % of the SAM). Other ranges are also possible.

In some embodiments, a SAM may comprise a species capable of capturing a first species (e.g., a target polypeptide such as a protein, a target polynucleotide, a target small molecule) that may include a functional group suitable for capturing the first species, such as a maleimide group, a biotin group, a streptavidin group, a neutravidin group, an alkyne group, an alkene group, an azide group, a n-hydroxysuccinimide (NHS) group, a dibenzocyclooctyl (DBCO) group, a nitriloacetic acid (NTA) group, a phosphonate group, a glutathione group, a benzylguanine group, a benzylcytosine group, and/or a chloroalkane group. Other functional groups are also possible. In some embodiments, the species capable of capturing the first species does not fragment appreciably under typical MALDI (e.g., MALDI-TOF) measurement conditions.

As described above, in some embodiments a SAM may comprise a standard species that may be used to normalize data arising from a MALDI (e.g., MALDI-TOF) measurement. The standard species may be present at a known concentration or percent density in the SAM and/or at a pre-determined concentration or pre-determined percent density in the SAM. In some embodiments, standard species may be present at a concentration in the SAM of greater than or equal to 0.001 mol % of the SAM, greater than or equal to 0.002 mol % of the SAM, greater than or equal to 0.005 mol % of the SAM, greater than or equal to 0.01 mol % of the SAM, greater than or equal to 0.02 mol % of the SAM, greater than or equal to 0.05 mol % of the SAM, greater than or equal to 0.1 mol % of the SAM, greater than or equal to 0.2 mol % of the SAM, greater than or equal to 0.5 mol % of the SAM, greater than or equal to 1 mol % of the SAM, greater than or equal to 2 mol % of the SAM, greater than or equal to 5 mol % of the SAM, greater than or equal to 10 mol % of the SAM, greater than or equal to 20 mol % of the SAM, or greater than or equal to 50 mol % of the SAM. In some embodiments, the standard species may be present at a concentration in the SAM of less than or equal to 100 mol % of the SAM, less than or equal to 50 mol % of the SAM, less than or equal to 20 mol % of the SAM, less than or equal to 10 mol % of the SAM, less than or equal to 5 mol % of the SAM, less than or equal to 2 mol % of the SAM, less than or equal to 1 mol % of the SAM, less than or equal to 0.5 mol % of the SAM, less than or equal to 0.2 mol % of the SAM, less than or equal to 0.1 mol % of the SAM, less than or equal to 0.05 mol % of the SAM, less than or equal to 0.02 mol % of the SAM, less than or equal to 0.01 mol % of the SAM, less than or equal to 0.005 mol % of the SAM, or less than or equal to 0.002 mol % of the SAM. Combinations of the above-referenced ranges are also possible (e.g., greater than or equal to 0.001 mol % of the SAM and less than or equal to 100 mol % of the SAM). Other ranges are also possible. In some embodiments, the standard species does not fragment appreciably under typical MALDI measurement conditions.

In some embodiments in which a SAM comprises a standard species, the standard species may have a molecular weight that is within a range that is advantageous for detecting binding between a first species (e.g., a target polypeptide such as a protein, a target polynucleotide, a target small molecule) and a second species (e.g., a small molecule, a polypeptide such as a protein, a polynucleotide). For example, the molecular weight may be similar to the molecular weight of the second species and/or may not overlap with the molecular weight of the second species. In some embodiments, the molecular weight of the standard species may be greater than or equal to 300 Da, greater than or equal to 500 Da, greater than or equal to 1 kDa, greater than or equal to 2 kDa, greater than or equal to 5 kDa, greater than or equal to 10 kDa, greater than or equal to 20 kDa, greater than or equal to 50 kDa, greater than or equal to 100 kDa, greater than or equal to 200 kDa, greater than or equal to 500 kDa, or greater than or equal to 1000 kDa. In some embodiments, the molecular weight of the standard species may be less than or equal to 1500 kDa, less than or equal to 1000 kDa, less than or equal to 500 kDa, less than or equal to 200 kDa, less than or equal to 100 kDa, less than or equal to 50 kDa, less than or equal to 20 kDa, less than or equal to 1 kDa, or less than or equal to 500 Da. Combinations of the above-referenced ranges are also possible (e.g., greater than or equal to 300 Da and less than or equal to 1500 kDa). Other ranges are also possible.

In some embodiments, a SAM may comprise a standard species that comprises an alkane group. In some embodiments, the alkane group is greater than or equal to 6 carbons long, greater than or equal to 7 carbons long, greater than or equal to 8 carbons long, greater than or equal to 9 carbons long, greater than or equal to 10 carbons long, or greater than or equal to 11 carbons long. In some embodiments, the alkane group is less than or equal to 12 carbons long, less than or equal to 11 carbons long, less than or equal to 10 carbons long, less than or equal to 9 carbons long, less than or equal to 8 carbons long, or less than or equal to 7 carbons long. Combinations of the above-referenced ranges are also possible (e.g., greater than or equal to 6 carbons long and less than or equal to 12 carbons long). Other ranges are also possible.

In some embodiments, a SAM may comprise a standard species that comprises a non-alkane group. In some embodiments, the non-alkane group may be a polar group. In some embodiments, the non-alkane group may comprise one or more repeat units. The polar group may comprise greater than or equal to 1 repeat unit, greater than or equal to 2 repeat units, greater than or equal to 3 repeat units, greater than or equal to 4 repeat units, greater than or equal to 5 repeat units, greater than or equal to 6 repeat units, or greater than or equal to 7 repeat units. The non-alkane group may comprise less than or equal to 8 repeat units, less than or equal to 7 repeat units, less than or equal to 6 repeat units, less than or equal to 5 repeat units, less than or equal to 4 repeat units, less than or equal to 3 repeat units, or less than or equal to 2 EG repeat units. Combinations of the above-referenced ranges are also possible (e.g., greater than or equal to 1 and less than or equal to 8 repeat units). Other ranges are also possible.

In some embodiments, the non-alkane group may comprise one or more ethylene glycol (EG) repeat units. The polar group may comprise greater than or equal to 1 EG repeat units, greater than or equal to 2 EG repeat units, greater than or equal to 3 EG repeat units, greater than or equal to 4 EG repeat units, greater than or equal to 5 EG repeat units, greater than or equal to 6 EG repeat units, or greater than or equal to 7 EG repeat units. The non-alkane group may comprise less than or equal to 8 EG repeat units, less than or equal to 7 EG repeat units, less than or equal to 6 EG repeat units, less than or equal to 5 EG repeat units, less than or equal to 4 EG repeat units, less than or equal to 3 EG repeat units, or less than or equal to 2 EG repeat units. Combinations of the above-referenced ranges are also possible (e.g., greater than or equal to 1 and less than or equal to 8 EG repeat units). Other ranges are also possible.

In some embodiments, a SAM may comprise a standard species that comprises a group capable of bonding and/or interacting with a support on which the SAM is disposed. Non-limiting examples of such groups include thiol groups and disulfide groups.

In some embodiments, a SAM may comprise a standard species that is an $(EG)_n$-alkane thiol or an $(EG)_n$-alkyl disulfide, where n is the number of repeat units of the EG group.

In embodiments in which the SAM is present, it may have any suitable thickness. In some embodiments, the thickness of the SAM is greater than or equal to 10 Angstroms, greater than or equal to 20 Angstroms, greater than or equal to 30 Angstroms, greater than or equal to 40 Angstroms, greater than or equal to 50 Angstroms, greater than or equal to 60 Angstroms, greater than or equal to 70 Angstroms, greater than or equal to 80 Angstroms, or greater than or equal to 90 Angstroms. In some embodiments, the thickness of the SAM is less than or equal to 100 Angstroms, less than or equal to 90 Angstroms, less than or equal to 80 Angstroms, less than or equal to 70 Angstroms, less than or equal to 60 Angstroms, less than or equal to 50 Angstroms, less than or equal to 40 Angstroms, less than or equal to 30 Angstroms, or less than or equal to 20 Angstroms. Combinations of the above-referenced ranges are also possible (e.g., greater than or equal to 10 Angstroms and less than or equal to 100 Angstroms). Other ranges are also possible.

As described above, in some embodiments a SAM may be disposed on a support. In some embodiments, the support may be electrically conductive. Non-limiting examples of suitable supports include metals (e.g., gold, titanium) and alloys (e.g., stainless steel).

As described above, certain embodiments may comprise applying a matrix to a SAM. In some embodiments, it may be advantageous for the matrix to not fragment appreciably under typical MALDI (e.g., MALDI-TOF) measurement conditions. In some embodiments, the matrix may comprise one or more of 9-aminoacridine, 4-aminoquinaldine, anthranilamide, (2E)-3-(9-anthryl)-2-cyanoacrylic acid, 4-bromo-alpha-cyanocinnamic acid, a mixture comprising 4-bromo-alpha-cyanocinnamic acid and 4-chloro-alpha-cyanocinnamic acid, a mixture comprising 4-bromo-alpha-cyanocinnamic acid and alpha-Cyano-2,4-difluorocinnamic acid, trans-2-[3-(4-tert-butylphenyl)-2-methyl-2-propenylidene]malononitrile, caffeic acid, 4-chloro-alpha-cyano-cinnamic acid, a mixture comprising 4-chloro-alpha-cyano-cinnamic acid and alpha-Cyano-2,4-difluorocinnamic acid, alpha-cyano-4-fluorocinnamic acid, alpha-cyano-4-hydroxycinnamic acid, a mixture comprising alpha-Cyano-4-hydroxycinnamic acid and alpha-cyano-2,4-difluorocinnamic acid and alpha-cyano-2,3,4,5,6-pentafluorocinnamic acid, (E)-2-cyano-3-(2-naphthyl)acrylic acid, alpha-cyano-2,3,4,5,6-pentafluorocinnamic acid, 1,5-diaminonaphthalene, 2',6'-dihydroxyacetophenone, 2,5-dihydroxybenzoic acid, 2,5-dihydroxybenzoic acid, trans-ferulic acid, 2-(4-hydroxyphenylazo)benzoic acid, 3-hydroxypicolinic acid, 9-nitroanthracene, sinapic acid, succinic acid, super-DHB, and 2',4',6'-trihydroxyacetophenone monohydrate.

In some embodiments, a matrix may be provided in a formulation comprising a solvent. In certain embodiments, the solvent may be an organic solvent such as acetonitrile and/or acetone. In some embodiments, the solvent may comprise water.

In some embodiments, methods for detecting binding between a first species and a second species are provided. The methods may comprise exposing the first species to a composition comprising the second species; capturing the first species on a self-assembled monolayer comprising a standard species; performing MALDI on the self-assembled monolayer to generate a signal from the second species and a signal from the standard species; and determining whether binding has occurred if a ratio of the signal from the second species to the signal from the standard species is greater than or equal to a cutoff value.

In some embodiments, methods for comparing a relative affinity of a first small molecule for a target polypeptide to a relative affinity of a second small molecule for the target polypeptide are provided. The methods may comprise exposing the target polypeptide to a composition comprising at least the first small molecule and the second small molecule; capturing the target polypeptide on a self-assembled monolayer comprising a standard species; performing MALDI on the self-assembled monolayer to generate a signal from the first small molecule, a signal from the second small molecule, and a signal from the standard species; and comparing a first ratio to a second ratio to determine a relative affinity of the first small molecule for the target polypeptide and the second small molecule for the target polypeptide, wherein the first ratio comprises a ratio of the signal from the first small molecule to the signal from the standard species, and the second ratio comprises a ratio of the signal from the second small molecule to the signal from the standard species.

In some embodiments, articles related to detecting binding between a first species and a second species are provided. The article may include a self-assembled monolayer comprising a standard species (e.g., a standard species that does not undergo appreciable fragmentation during MALDI), a first species captured on the self-assembled monolayer, and a second species bound to the first species. In some embodiments, a third species may be bound to the first species.

In some embodiments, methods for performing quality control on a MALDI instrument are provided. The methods may comprise performing a MALDI measurement on a self-assembled monolayer comprising a known concentration of a standard species to generate a signal from the standard species and determining whether an abnormality has occurred if the signal from the standard species is outside of a pre-determined range.

In some embodiments as described above and/or herein, the first species is at least one of a target polypeptide, a target protein, a target oligonucleotide, a target DNA molecule, and a target RNA molecule.

In some embodiments as described above and/or herein, the second species is at least one of a polypeptide, a protein, an oligonucleotide, a DNA molecule, an RNA molecule, and a small molecule.

In some embodiments as described above and/or herein, the composition comprises a third species.

In some embodiments as described above and/or herein, the third species is at least one of a polypeptide, a protein, an oligonucleotide, a DNA molecule, an RNA molecule, and a small molecule.

In some embodiments as described above and/or herein, the wt % of the first small molecule in the composition is equal to the wt % of the second small molecule in the composition.

In some embodiments as described above and/or herein, a ratio of the wt % of the second species in the composition to the third species in the composition is greater than or equal to 0.5 and less than or equal to 2.

In some embodiments as described above and/or herein, the target polypeptide is a protein.

In some embodiments as described above and/or herein, the target polypeptide is a biotinylated protein.

In some embodiments as described above and/or herein, the target polypeptide comprises BACE.

In some embodiments as described above and/or herein, the target polypeptide comprises DLK.

In some embodiments as described above and/or herein, the target polypeptide is exposed to the composition prior to being captured on the self-assembled monolayer.

In some embodiments as described above and/or herein, the target polypeptide is exposed to the composition in solution.

In some embodiments as described above and/or herein, the target polypeptide is exposed to the composition after being captured on the self-assembled monolayer.

In some embodiments as described above and/or herein, the composition comprises a surfactant.

In some embodiments as described above and/or herein, the composition comprises an agent that reduces non-specific binding.

In some embodiments as described above and/or herein, a method further comprises washing the self-assembled monolayer after capturing the target polypeptide.

In some embodiments as described above and/or herein, a method further comprises washing the self-assembled monolayer after exposing the target polypeptide to the composition.

In some embodiments as described above and/or herein, a method further comprises applying a matrix to the self-assembled monolayer.

In some embodiments as described above and/or herein, the matrix does not undergo appreciable fragmentation during MALDI.

In some embodiments as described above and/or herein, the self-assembled monolayer comprises at least one of streptavidin, neutravidin, a maleimide group, biotin, an alkyne group, an alkene group, an azide group, n-hydroxysuccinimide, dibenzocyclooctyl, nitriloacetic acid, glutathione, a phosphonate, benzylguanine, benzylcytosine, and a chloroalkane.

In some embodiments as described above and/or herein, the self-assembled monolayer comprises a standard species.

In some embodiments as described above and/or herein, the standard species is present at a known concentration within the monolayer.

In some embodiments as described above and/or herein, the standard species does not undergo appreciable fragmentation during MALDI.

In some embodiments as described above and/or herein, the standard species comprises an (EG)n-alkane thiol or an (EG)n-alkyl disulfide, wherein EG is ethylene glycol.

In some embodiments as described above and/or herein, binding comprises non-covalent binding.

In some embodiments as described above and/or herein, a method further comprises determining the amount of binding that has occurred based on an area under a curve of a normalized small molecule signal or based on a peak intensity of the normalized small molecule signal.

In some embodiments as described above and/or herein, the composition comprises a control species.

In some embodiments as described above and/or herein, a method further comprises determining that an abnormality has occurred if a signal from the control species is outside of a pre-determined range.

Example 1

This example describes an inventive screening format for small molecule binding using Self-Assembled Monolayers and matrix-assisted laser Desorption Ionization (SAMDI) technology. As described below, target proteins undergo the two following steps in either order: binding one or more small molecules and undergoing affinity capture on a self-assembled monolayer (SAM). Then, the captured protein, bound small molecule(s), and monolayer are subject to MALDI-TOF analysis, where the identities of any bound small molecules may be identified by their masses and the relative amount of each bound small molecule may be determined by their relative areas under the curve (AUCs) in the measured MALDI-TOF spectrum. The method described in this Example may have one or more features that are advantageous for detecting small molecule binding.

For example, capturing target proteins by uniformly saturating a SAM surface may minimize crystallization "hot spots" and reduce shot-to-shot variability. As another example, the use high-resolution MALDI-TOF may result in limited interference from salt, detergent, and matrix during small molecule detection. Certain embodiments described below which relate to a pooled library format may allow for high-throughput of MALDI-TOF-based screening at a variety of enzyme activities. The method described below may also allow the determination of relative binding affinity rank ordering from a pool of small molecules, which may correlate with potency data that could be obtained from a biochemical assay.

Materials and Methods

Matrix Selection for Small Molecule Detection

Figure 3A:
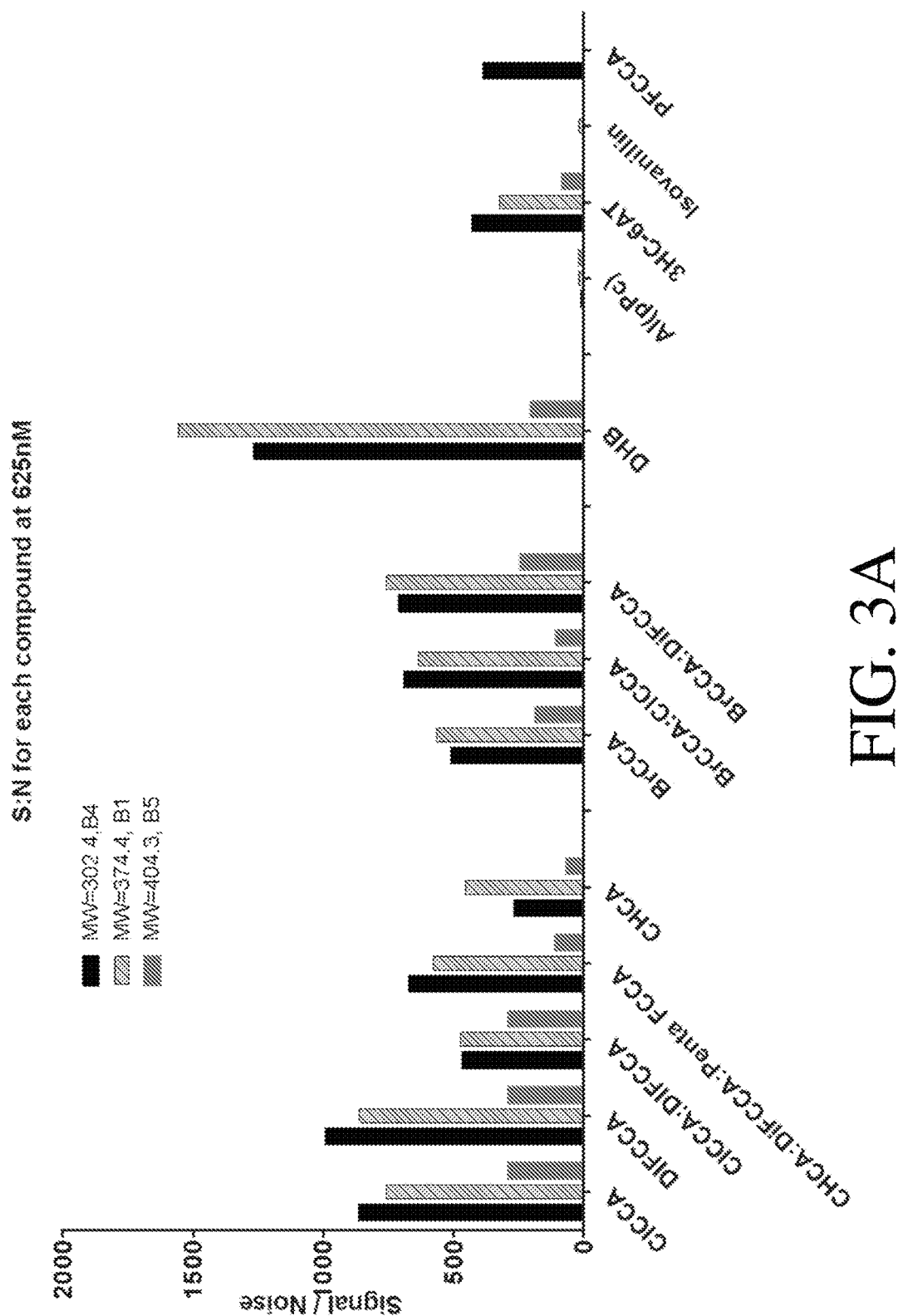
FIG. 3A shows signal to noise ratios for several matrix materials, according to some embodiments.
Figure 3B:
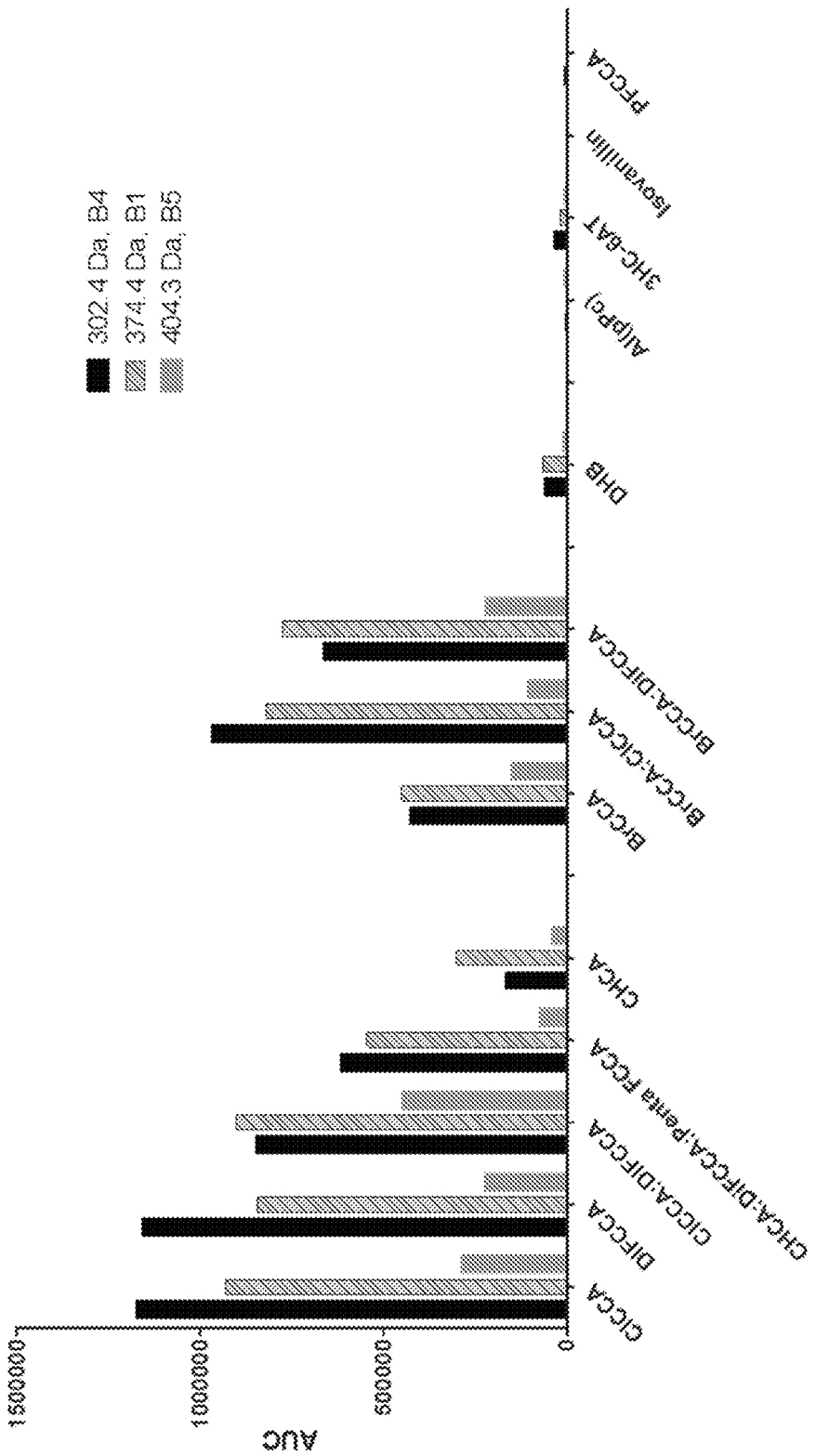
FIG. 3B shows areas under the curve for several matrix materials, according to some embodiments.

Three kinase inhibitors with molecular weights (MW) in the 200-600 Da range were prepared as solutions in dimethyl sulfoxide (DMSO) with concentrations between 20 and 0.625 μM. The compounds were tested with a panel of 13 matrices (Table 1; FIGS. 3A and 3B) by diluting the compound solution with an equal volume of matrix. One μL of each solution comprising a mixture of a compound and the matrix was then spotted onto a MALDI target plate. Matrices which resulted in appreciable signal and high signal to noise ratios for the representative compounds were considered acceptable.

Protein and Compounds to Minimize Non-Selective Binding

Figure 4A:
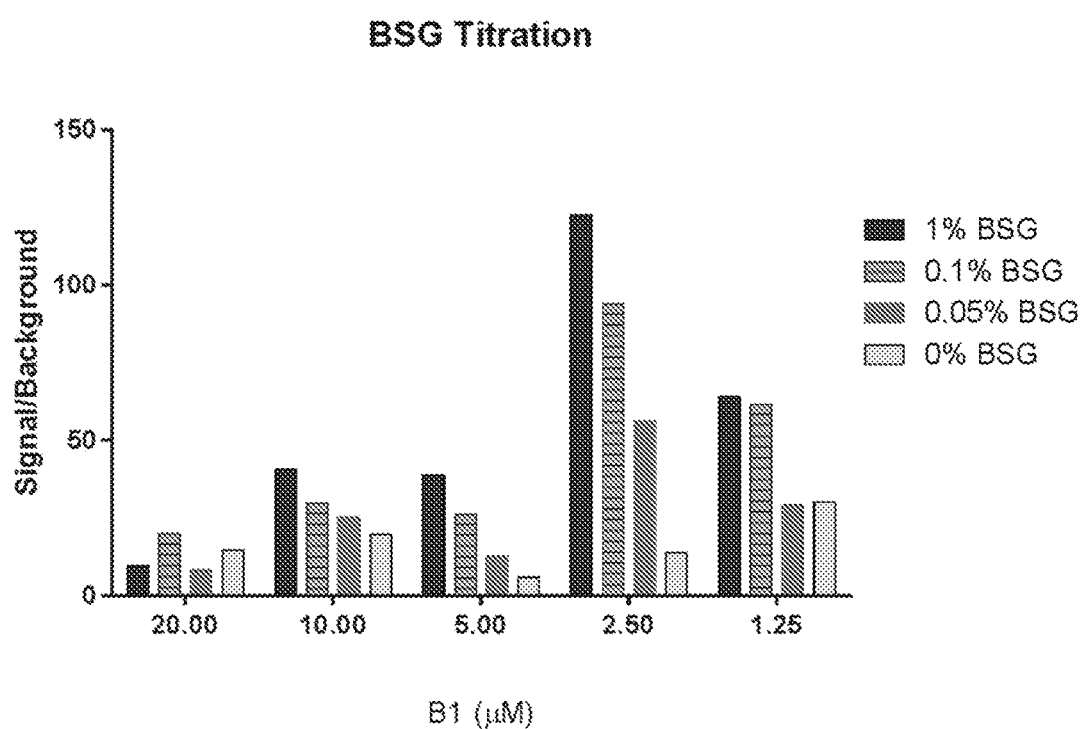
FIG. 4A shows signal to background ratios for a species in a composition comprising varying amounts of bovine skin gelatin, according to some embodiments.
Figure 4B:
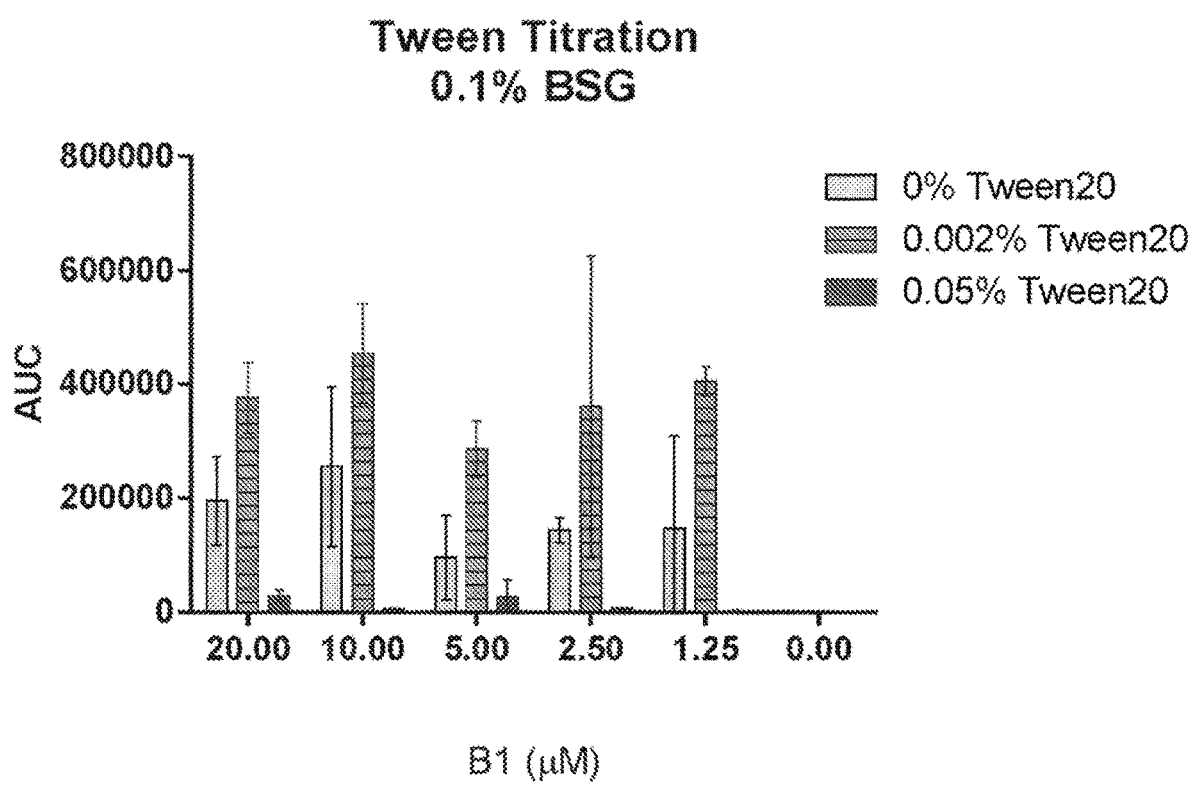
FIG. 4B shows areas under the curve for a species in a composition comprising varying amounts of Tween20, according to some embodiments.

Biotinylated protein, β-secretase (BACE) and the desired concentration of small molecule(s) to be bound were mixed in an aqueous buffer containing 20 mM sodium acetate at pH 4.4, 0.002 wt % Tween 20, and 0.1 wt % Bovine Skin Gelatin (BSG, Sigma Aldrich, St. Louis, MO) for BACE. Dual Leucine Zipper Kinase (DLK, MAP3K12, Carna Biosciences, Natick, MA) and the desired concentration of small molecule(s) were mixed in an aqueous Tris buffer at pH 8, 0.002 wt % Tween 20, and a range of 1-0.25 wt % dimethyl sulfoxide (DMSO). The concentrations of BSG and Tween were selected in order to reduce non-specific small molecule binding and to reduce spreading on the SAMDI plate (FIGS. 4A and 4B).

Single Compound Assays

Small molecules were bound to target proteins either in solution phase or in solid phase. The solution phase method was used for individual compound binding $EC_{50}$ determination, plate uniformity determination, and pooled compound experiments. In solution phase binding, eight different 1 μM biotinylated-protein sample in assay buffer were incubated at room temperature for up to 30 minutes with eight different solutions comprising the small molecule to be bound at varying concentrations ranging from 40 μM to 80 μM in aqueous buffer. After incubation, the solutions were transferred to a 384-spot SAMDI plate that included a monolayer of neutravidin immobilized onto a self-assembled monolayer comprising 3 wt % (Biotin-Ethylene Glycol)$_6$-SH and 97 wt % (Ethylene Glycol)$_3$-SH. Biotinylated-proteins and any small molecules bound thereto were captured by the monolayer during this step. In solid phase binding, 1 μM biotinylated-BACE protein was captured by the neutravidin-coated SAMDI plate prior to exposure to any small molecules to be bound. The SAMDI plate was then washed with assay buffer and exposed to solutions comprising small molecules to be bound.

TABLE 1

| Matrix No. | Matrix | Molecular weight (Da) | Stock concentration (mg/mL) | Solvent |
|---|---|---|---|---|
| 1 | 4-chloro-α-cyanocinnamic acid (CICCA) | 207.61 | 30 | 80 wt % acetonitrile/ 20 wt % water |
| 2 | α-cyano-2,4-difluorocinnamic acid (DIFCCA) | 209.15 | 30 | 80 wt % acetonitrile/ 20 wt % water |
| 3 | CICCA:DIFCCA | 207.61; 209.15 | 30 | 80 wt % acetonitrile/ 20 wt % water |
| 4 | α-cyano-4-hydroxycinnamic acid, α-cyano-2,4-difluorocinnamic acid, and α-cyano-2,3,4,5,6-pentafluorocinnamic acid mixture | 189.7; 209.15; 263.12 | 30 | 70 wt % acetonitrile/ 30 wt % water |
| 5 | α-cyano-4-hydroxycinnamic acid (CHCA) | 189.2 | 30 | 80 wt % acetonitrile/ 20 wt % water |
| 6 | 4-bromo-α-cyanocinnamic acid (BrCCA) | 252.06 | 30 | 80 wt % acetonitrile/ 20 wt % water |
| 7 | BrCCA:CICCA | 252.06; 209.15 | 30 | 80 wt % acetonitrile/ 20 wt % water |
| 8 | BrCCA:DiFCCA | 252.06; 209.15 | 30 | 80 wt % acetonitrile/ 20 wt % water |
| 9 | 2,5-dihydroxybenzoic acid (DHB) | 154.12 | 30 | 80 wt % acetonitrile/ 20 wt % water |
| 10 | Aluminum phenylthio pthalocyanine (Al (pPc)) | 1007.6 | 30 | 80 wt % acetonitrile/ 20 wt % water |
| 11 | 3-hydroxycoumarin and 6-aza-2-thiothymine (3HC-6AT) | 162.14; 143.17 | 30 | 80 wt % acetonitrile/ 20 wt % water |
| 12 | Isovanillin | 152.15 | 30 | 80 wt % acetonitrile/ 20 wt % water |
| 13 | α-cyano-2,3,4,5,6-pentafluorocinnamic acid (PFCCA) | 263.12 | 30 | 80 wt % acetonitrile/ 20 wt % water |

Pooled Assays

Small molecules with a range of inhibitory activities were synthesized and pooled at 10 mM in DMSO to yield a final concentrations of 10 μM for assays with BACE and 5 μM for assays with DLK for each individual compound. Mixtures of either 1 μM biotinylated-BACE with the 10 μM compound pools or 650 nM biotinylated-DLK with the 5 μM compound pools were incubated in a humidified chamber at room temperature for up to 30 minutes. Then 2.5 μL of each solution was applied to a 384-spot SAMDI plate that included a monolayer of neutravidin immobilized onto a self-assembled monolayer comprising 3 wt % (Biotin-Ethylene Glycol)$_6$-SH and 97 wt % (Ethylene Glycol)$_3$-SH. After this step, the SAMDI plate was washed gently three times with 20 mL of water (for a total 60 mL of water) and then dried using compressed air. Next, a matrix (consisting of a mixture of 20 mg/mL α-Cyano-4-hydroxycinnamic acid (CHCA, Sigma Aldrich, St. Louis, MO) in acetonitrile, 25 mg/mL dihydroammonium citrate (DHAC, Sigma Aldrich, St. Louis, MO), 0.3% trifluoroacetic acid unless otherwise specified) was applied by dispensing approximately 50 nL of the matrix on each spot on the SAMDI plate.

Mass Spectrometry Detection of Small Molecules Bound to Target Proteins on SAMDI Plates:

An ABSCIEX 5800 MALDI TOF-TOF (AB Sciex, Framingham, MA) or a Bruker UltraFleXtreme MALDI TOF-TOF (Bruker Daltonics, Bremen, Germany) was used to acquire data in the 100-600 m/z range in reflector positive mode. For the AB Sciex 5800 MALDI TOF-TOF mass spectrometer, a 400 Hz YAG laser (power 4000, 600 laser shots) was used. For the Bruker UltraFleXtreme MALDI-TOF-TOF mass spectrometer, a 1 kHz laser (66% power, 500 laser shots) was used.

Binding of the small molecules was quantitated by normalizing the area under the curve (AUC) of the small molecule compound peak to the AUC of the (Ethylene Glycol)$_3$-SH (EG3 thiol) monolayer component with a molecular weight (MW) 335.2 Da. The normalized AUC data was analyzed with Genedata Expressionist® software (Genedata, Basel, Switzerland) in batch load mode. Bound small molecules were identified and annotated in the spectra based by comparing experimental mass to compound masses and chemical formulas in the Genedata Expressionist® database. AUCs of small molecules within a given pool of were determined for experiments that were performed as described above and for control experiments where the small molecules were incubated in the absence of a target protein. Small molecules with equivalent signal in the presence and absence of the target protein were identified as nonspecific compound binders and eliminated as hits.

Results and Discussion

SAMDI Workflow for Affinity Capture and MS Detection

Figure 5A:
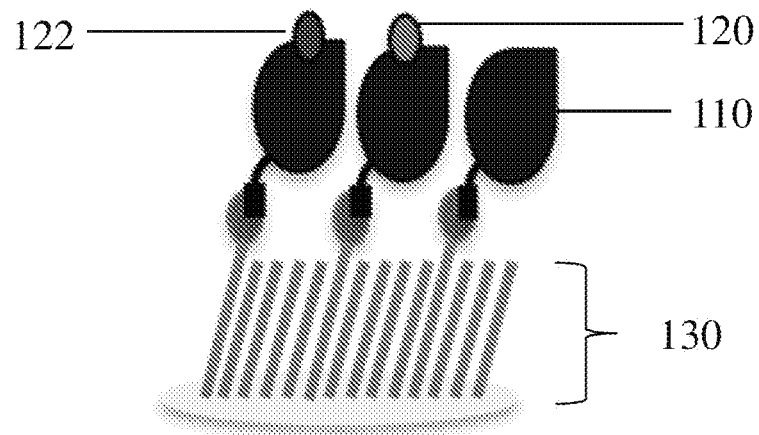
FIG. 5A shows a schematic depiction of capture of a first species bound to a second species and a first species bound to a third species on a self-assembled monolayer, according to some embodiments.
Figure 5B:
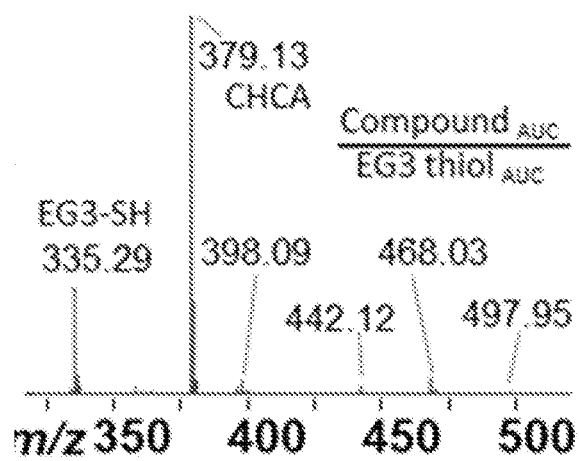
FIG. 5B shows normalized areas under the curve for several species captured on a self-assembled monolayer, according to some embodiments.

The schematic of the SAMDI workflow to identify binding of small molecules to a protein target is shown in FIGS. 5A and 5B. The first step involved incubating a composition comprising a second species 120 (in this case a small molecule) and optionally a third species 122 with a first species 110 (in this case a biotinylated protein) in solution to allow complex formation. The solution was then spotted onto neutravidin-coated SAMDI plates 130 as described above for affinity capture of the biotinylated protein with bound and unbound compounds. After this step, the plates were washed, a matrix was applied to the plates, and then MALDI-TOF was employed to detect the amount and type of small molecules that had bound to the protein during incubation. After the MALDI-TOF experiment was performed, the AUC of each signal from a bound small molecule was divided by the AUC obtained from the standard species on the SAMDI plate (in this case the EG3-thiol molecule) to obtain a normalized AUC for each bound small molecule signal.

Matrix Selection for Small Molecule MALDI-TOF Detection

Representative MALDI mass spectra of the CHCA matrix alone and of the CHCA matrix co-crystallized with a five-component small molecule mixture in which each of the components was present at a concentration of 2 µM each during crystallization are shown in FIG. 5. To assess the impact of different matrices on the ability of MALDI MS to detect small molecules, a panel of 13 matrices were evaluated for low background and high signal to noise (S/N) ratio for the low mass range (FIG. 3A). Eight of the thirteen matrices tested yielded S/N>100 and mean AUC>5×10$^5$ for the tested small molecules at concentrations as little as 625 nM (FIG. 3B). 2,5-DHB showed low background in the low mass range; however, the signal intensity for each small molecule was also low for this matrix. On the other hand, the CHCA matrix achieved a good balance between S/N and total compound intensity.

Solution Vs Solid Phase Capture for SAMDI Small Molecule Binding

In the SAMDI small molecule binding assay workflow, individual small molecules known to bind and inhibit BACE either in solution phase in solid phase were studied first in order to determine the best format for retaining specific small molecules binding to a protein target. In solution phase binding, the small molecules and BACE were incubated to form complexes in an assay plate and then transferred to a neutravidin-coated SAMDI plate followed by a washing step. For solid phase binding, the biotinylated-BACE was first bound directly onto a neutravidin coated SAMDI plate, followed by a washing step that occurred before exposure of BACE to the small molecules.

Figure 6A:
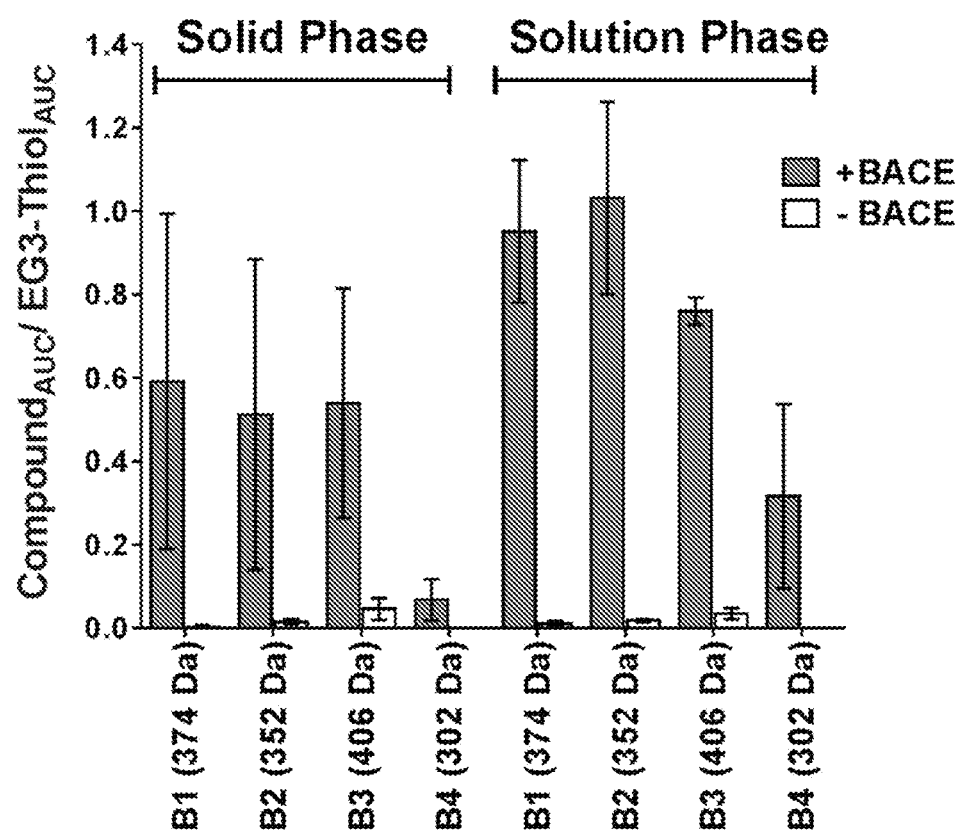
FIG. 6A shows normalized areas under the curve for several species captured on a self-assembled monolayer after exposure of the species to a target species prior to capture and after capture of the target species prior to exposure to the species, according to some embodiments.

Small molecule solution phase binding was compared to small molecule solid phase binding for four small molecules (each with a sample size of four). As shown in FIG. 6A, small molecules that were bound in the solution phase had a signal that was roughly 2-fold higher than small molecules that were bound in the solid phase.

Compound Dose Response Detected by SAMDI Small Molecule Assay

Figure 6B:
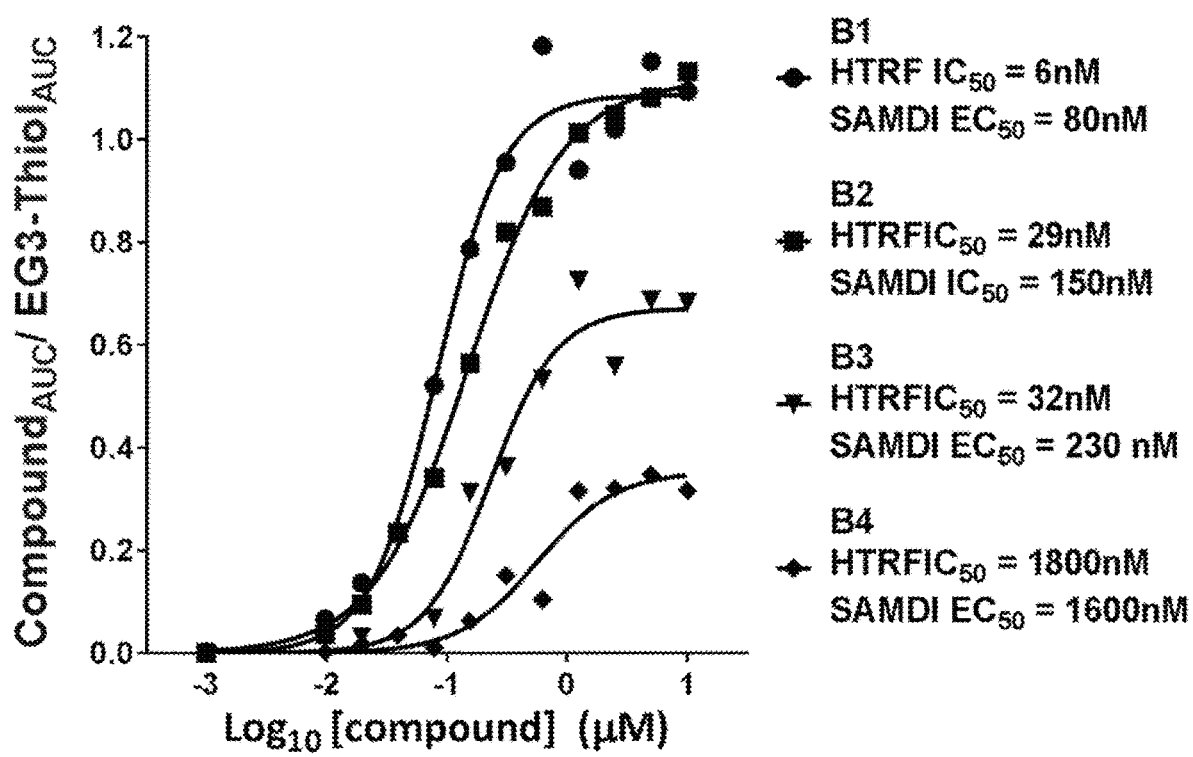
FIG. 6B shows normalized areas under the curve for several species captured on a self-assembled monolayer as a function of concentration in a composition, according to some embodiments.

Using the solution phase binding method described above, four small molecules from a chemical series with varying affinities for BACE were titrated individually, incubated with biotinylated-BACE in solution, captured on SAMDI plates, and analyzed using MALDI-TOF. The relative rankings of the IC$_{50}$ values for the four small molecules found at the conclusion of this process (determined based on measurements taken for four samples of each small molecule at each titration level) were similar to the relative rankings of BACE-HTRF activity measured by biochemical assay techniques. The percent of each small molecule bound at a 10 µM concentration also correlated with the biochemical activity data. The small molecule that bound most weakly in a biochemical HTRF assay, B4, which displayed an IC$_{50}$ of 1.8 µM, showed a percent bound of 25% at 10 µM and an EC$_{50}$ of 1.6 µM after SAMDI capture. The small molecule that bound most strongly in the biochemical HTRF assay, B1, which displayed an IC$_{50}$ of 6 nM, showed a percent bound of 100% at 10 µM and an EC$_{50}$ value of 80 nM (the highest of any of the four small molecules) after SAMDI capture (FIG. 6B).

Plate Uniformity

Figure 6C:
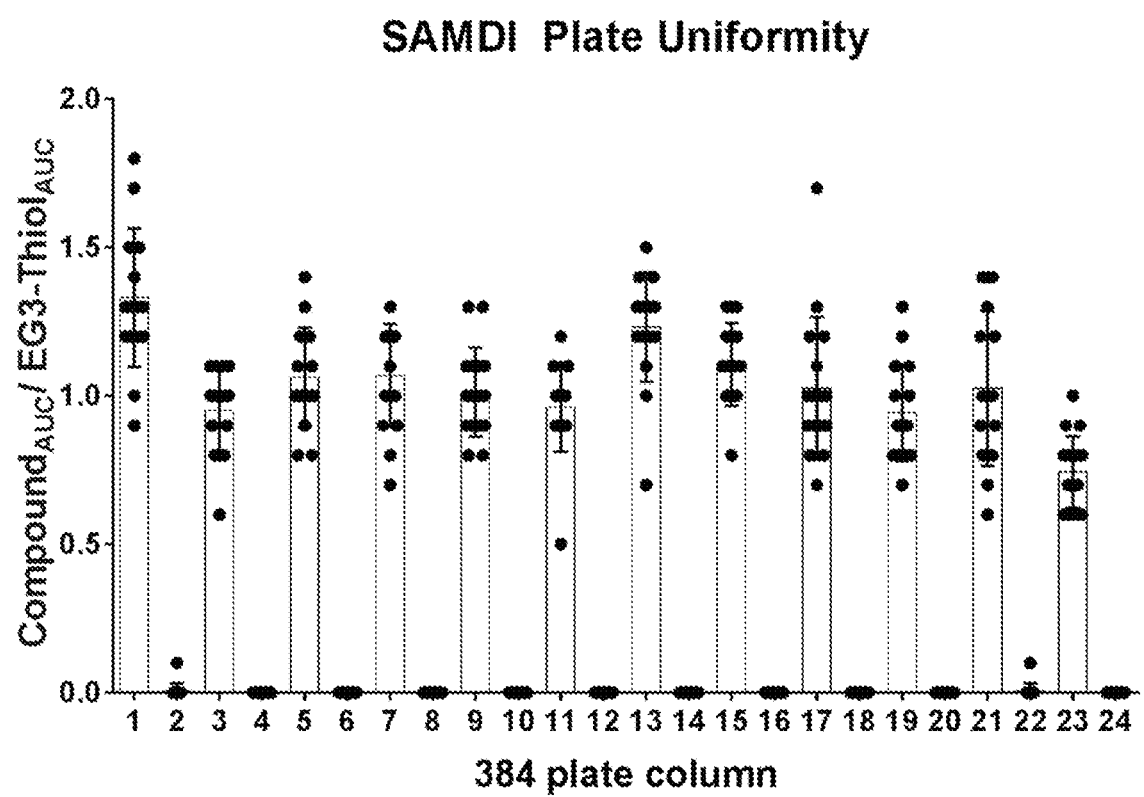
FIG. 6C shows normalized areas under the curve of several species in different locations on a SAMDI plate, according to some embodiments.

To test the data uniformity of the SAMDI plates used herein, a 384-spot SAMDI plate was spotted with alternating columns of samples comprising both 1 µM of B1 (MW=374 Da, HTRF IC$_{50}$=6 nM) and 1 µM of biotinylated-BACE protein and samples comprising 1 µM of B1 but lacking the biotinylated-BACE protein (FIG. 6C). The mean compound B1 AUC for samples without BACE was less than 1000, consistent with the absence of small molecule detection. In contrast, samples with BACE gave compound mean AUC values of 3×10$^5$ for compound B1, a 300-fold small molecule signal increase. Data uniformity was enhanced by normalizing the measured small molecule signal to the measured signal from the EG3 thiol present in the SAM. After EG3 thiol normalization (FIG. 6C), the % CV of the samples with BACE decreased from 48% to 22% and the S/N increased from 300-fold to 400-fold.

The EG3 thiol may also serve as a quality control tool to assess assay performance over time. This material is present at a uniform concentration across the SAMDI plate, and so tracking its AUC over time can show trends both intra- and inter-SAMDI plate which indicate changes in the detection sensitivity over the duration of a screen. This set of data can also serve as an early indicator that source cleaning may be needed or recommended. If used in parallel with control compounds, the normalized data could also be used to monitor for potential complications with the automation process during sample preparation, such as incorrect transfer of analytes from the assay plate to the SAMDI plate.

Proof-of-Concept Application of SAMDI in Pooled Compound Binding Screen

Figure 7A:
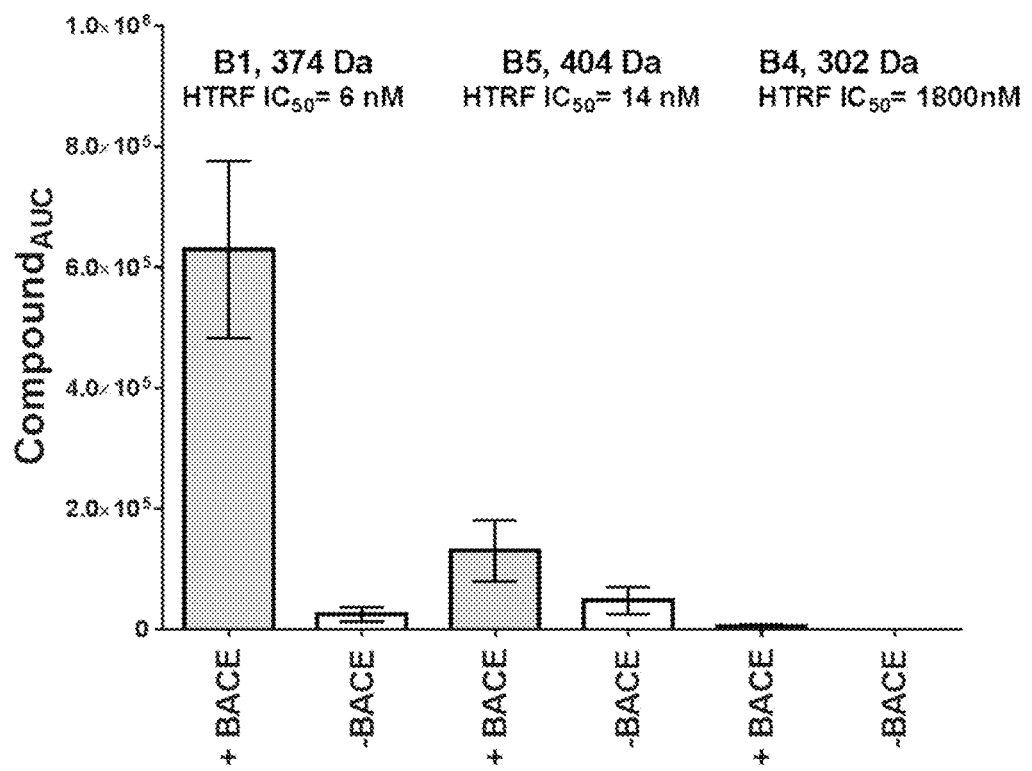
FIG. 7A shows areas under the curve for several species in the presence and absence of BACE, according to some embodiments.

Proof-of-concept experiments were performed by pooling together three small molecules with varying inhibitory potencies against BACE, incubating the pool with biotinylated BACE, capturing the biotinylated BACE and any small molecule bound thereto on a SAMDI plate, and then performing MALDI-TOF to determine the AUCs for each small molecule. The AUC rank ordering of small molecules showed good agreement with measured HTRF activity data (FIG. 7A). Small molecules with lower measured $IC_{50}$ values had larger measured AUCs compared than small molecules with higher measured $IC_{50}$ values. The pooled detection format was capable of detecting potent inhibitors in the hundreds of nM range with 25-fold signal over the control samples which lacked a target protein.

Figure 7B:
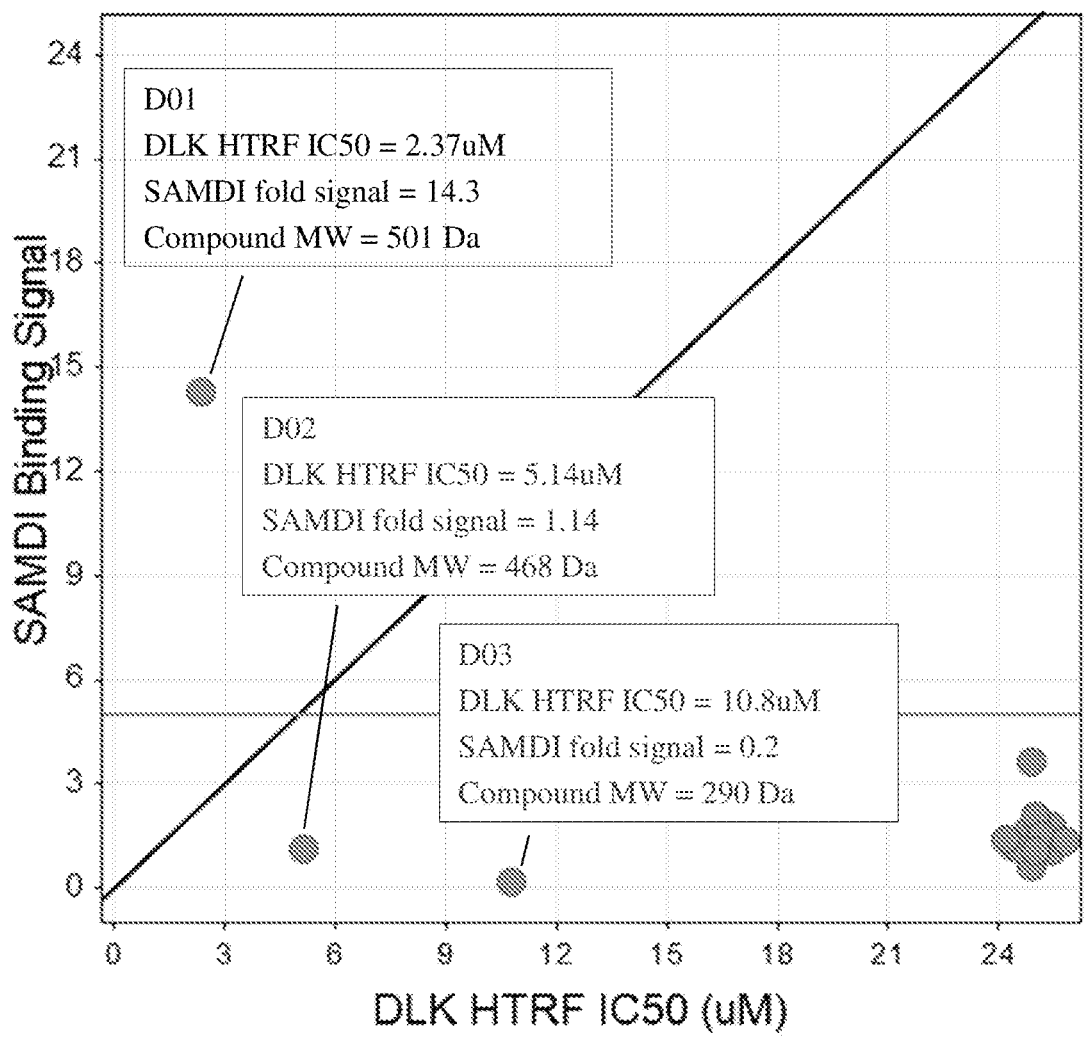
FIG. 7B shows SAMDI binding signal as a function of DLK HTRF $IC_{50}$ for several species, according to some embodiments.

Further experiments were formed which mimicked the conditions of a screen against a random and unbiased library, in which 650 nM biotinylated-DLK was incubated with a pool including three small molecules that are ATP-competitive DLK inhibitors (D01, D02, and D03). These small molecules displayed good ionization efficiency for MALDI-TOF and had weak biochemical $IC_{50}$ values of 2 μM for D01, 5 μM for D02, and 10 μM for D03. The pool also included twenty inactive small molecules, each of which has $IC_{50}$ values of greater than 25 μM. The concentration of each compound in the pool was 5 μM. Small molecule D01 (DLK-HTRF $IC_{50}$=2 μM) showed a 15-fold larger AUC when incubated with biotinylated-DLK than when incubated without biotinylated-DLK and so it was identified as a binder for this protein (FIG. 7B). The two weaker compounds with DLK HTRF $IC_{50}$=5 μM and 10 μM did not show a significantly larger when incubated with biotinylated-DLK than when incubated without DLK. This result was consistent with the hypothesis that the DLK protein was fully occupied by the most potent inhibitor in the pool, given that the more weakly inhibiting small molecules present were also known to bind to the same site of the protein and were not detected as binders.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for detecting binding between a first species and a second species, comprising:
    exposing the first species to a composition comprising the second species;
    capturing the first species on a self-assembled monolayer, wherein the self-assembled monolayer comprises a standard species prior to the capture of the first species thereon;
    performing MALDI on the self-assembled monolayer to generate a signal from the second species and a signal from the standard species;
    measuring the signal from the second species;
    measuring the signal from the standard species; and
    determining whether binding has occurred if a ratio of the signal from the second species to the signal from the standard species is greater than or equal to a cutoff value.

2. A method as in of claim 1, wherein the first species is at least one of a polypeptide, a protein, an oligonucleotide, a DNA molecule, and an RNA molecule.

3. A method as in claim 1, wherein the second species is at least one of a polypeptide, a protein, an oligonucleotide, a DNA molecule, an RNA molecule, and a molecule having a molecular weight of not more than 1,000 g/mol.

4. A method as in claim 1, wherein the composition comprises a third species.

5. A method as in claim 4, wherein the third species is at least one of a polypeptide, a protein, an oligonucleotide, a DNA molecule, an RNA molecule, and a molecule having a molecular weight of not more than 1,000 g/mol.

6. A method as in claim 4, wherein a ratio of the wt % of the second species in the composition to the third species in the composition is greater than or equal to 0.5 and less than or equal to 2.

7. A method as in claim 1, wherein the composition comprises a surfactant.

8. A method as in claim 1, wherein the composition comprises an agent that reduces non-specific binding.

9. A method as in claim 1, further comprising applying a matrix to the self-assembled monolayer.

10. A method as in claim 9, wherein the matrix does not undergo fragmentation during MALDI-TOF.

11. A method as in claim 1, wherein the self-assembled monolayer comprises at least one of streptavidin, neutravidin, a maleimide group, biotin, an alkyne group, an alkene group, an azide group, n-hydroxysuccinimide, dibenzocyclooctyl, nitriloacetic acid, glutathione, a phosphonate, benzylguanine, benzylcytosine, and a chloroalkane.

12. A method as in claim 1, wherein the standard species is present at a known concentration within the monolayer.

13. A method as in claim 1, wherein the standard species does not undergo fragmentation during MALDI-TOF.

14. A method as in claim 1, wherein the standard species comprises an $(EG)_n$-alkane thiol or an $(EG)_n$-alkyl disulfide, wherein EG is ethylene glycol.

15. A method as in claim 1, wherein the binding comprises non-covalent binding.

16. A method as in claim 1, further comprising measuring a signal from a molecule having a molecular weight of not more than 1,000 g/mol, further comprising normalizing the signal from the molecule having the molecular weight of not more than 1,000 g/mol by the signal from the standard species, and further comprising determining the amount of binding that has occurred based on an area under a curve of a normalized signal from the molecule having the molecular weight of not more than 1,000 g/mol or based on a peak intensity of the normalized signal from the molecule having the molecular weight of not more than 1,000 g/mol.

17. A method as in claim 1, wherein the composition comprises a control species.

18. A method as in claim 17, further comprising measuring a signal from a control species, and further comprising determining that an abnormality has occurred if the signal from the control species is outside of a pre-determined range.

19. A method as in claim 1, further comprising washing the self-assembled monolayer after capturing the first species.

20. A method for detecting binding between a first species and a second species, comprising:
    exposing the first species to a composition comprising the second species;
    capturing the first species on a self-assembled monolayer, wherein the self-assembled monolayer comprises a standard species, and wherein the standard species comprises a group capable of bonding and/or interacting with a support on which the self-assembled monolayer is disposed and/or that is bonded to and/or interacting with the support on which the self-assembled monolayer is disposed;
    performing MALDI on the self-assembled monolayer to generate a signal from the second species and a signal from the standard species;
    measuring the signal from the second species;
    measuring the signal from the standard species; and
    determining whether binding has occurred if a ratio of the signal from the second species to the signal from the standard species is greater than or equal to a cutoff value.

* * * * *